US012808085B2

(12) United States Patent
Ye

(10) Patent No.: US 12,808,085 B2
(45) Date of Patent: Nov. 24, 2026

(54) UMI AND APPLICATION THEREOF, MOLECULAR IDENTIFIER GROUP, ADAPTER, ADAPTER LIGATION REAGENT, KITS, METHOD FOR CONSTRUCTING DNA LIBRARY AND METHOD FOR SEQUENCING GENE

(71) Applicants: CHENGDU BOE OPTOELECTRONICS TECHNOLOGY CO., LTD., Sichuan (CN); BOE TECHNOLOGY GROUP CO., LTD., Beijing (CN)

(72) Inventor: Bangquan Ye, Beijing (CN)

(73) Assignees: CHENGDU BOE OPTOELECTRONICS TECHNOLOGY CO., LTD., Chengdu (CN); BEIJING BOE TECHNOLOGY DEVELOPMENT CO., LTD., Beijing (CN)

( * ) Notice: Subject to any disclaimer, the term of this patent is extended or adjusted under 35 U.S.C. 154(b) by 1015 days.

(21) Appl. No.: 17/912,373

(22) PCT Filed: Nov. 29, 2021

(86) PCT No.: PCT/CN2021/134159
§ 371 (c)(1),
(2) Date: Sep. 16, 2022

(87) PCT Pub. No.: WO2023/092601
PCT Pub. Date: Jun. 1, 2023

(65) Prior Publication Data
US 2024/0209349 A1 Jun. 27, 2024

(51) Int. Cl.
*C40B 40/06* (2006.01)
*C12N 15/10* (2006.01)

(52) U.S. Cl.
CPC .......... *C40B 40/06* (2013.01); *C12N 15/1065* (2013.01)

(58) Field of Classification Search
None
See application file for complete search history.

(56) References Cited

U.S. PATENT DOCUMENTS

2015/0072344 A1 3/2015 Wiley
2019/0194648 A1 6/2019 Wang et al.

FOREIGN PATENT DOCUMENTS

| | | | |
|---|---|---|---|
| CN | 108300716 | A | 7/2018 |
| CN | 108913753 | A | 11/2018 |
| CN | 109486811 | A | 3/2019 |
| CN | 109576347 | A | 4/2019 |
| CN | 111020711 | A | 4/2020 |
| CN | 111471754 | A | 7/2020 |
| CN | 113502287 | A | 10/2021 |
| WO | 2016049929 | A1 | 4/2016 |
| WO | 2021227129 | A1 | 11/2021 |

OTHER PUBLICATIONS

Yik et al. (Jan. 26, 2021) Journal of Pharmaceutical and Biomedical Analysis vol. 196 article 113920 pp. 1 to 6 (Year: 2021).*

* cited by examiner

*Primary Examiner* — Christian C Boesen
(74) *Attorney, Agent, or Firm* — XSENSUS LLP

(57) ABSTRACT

A unique molecular identifier (UMI) molecular tag includes at least one random base and at least one fixed base.

12 Claims, 6 Drawing Sheets

Specification includes a Sequence Listing.

SEQUENCE LISTING

```
<160> NUMBER OF SEQ ID NOS: 390

<210> SEQ ID NO 1
<211> LENGTH: 72
<212> TYPE: DNA
<213> ORGANISM: Artificial Sequence
<220> FEATURE:
<223> OTHER INFORMATION: made in laboratory
<220> FEATURE:
<221> NAME/KEY: misc_feature
<222> LOCATION: (26)..(33)
<223> OTHER INFORMATION: n is a, c, g, or t
<220> FEATURE:
<221> NAME/KEY: misc_feature
```

<222> LOCATION: (66)..(66)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t

<400> SEQUENCE: 1
aatgatacgg cgaccaccga gatctnnnnn nnnacactct ttccctacac gacgctcttc 60
cgatcnagnc tn 72

<210> SEQ ID NO 2
<211> LENGTH: 71
<212> TYPE: DNA
<213> ORGANISM: Artificial Sequence
<220> FEATURE:
<223> OTHER INFORMATION: made in laboratory
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (41)..(48)
<223> OTHER INFORMATION: n is a, c, g, or t

<400> SEQUENCE: 2
nagnctngat cggaagagca cacgtctgaa ctccagtcac nnnnnnnnat ctcgtatgcc 60
gtcttctgct t 71

<210> SEQ ID NO 3
<211> LENGTH: 7
<212> TYPE: DNA
<213> ORGANISM: Artificial Sequence
<220> FEATURE:
<223> OTHER INFORMATION: made in laboratory

<400> SEQUENCE: 3 aagacta 7

<210> SEQ ID NO 4
<211> LENGTH: 7
<212> TYPE: DNA
<213> ORGANISM: Artificial Sequence
<220> FEATURE:
<223> OTHER INFORMATION: made in laboratory

<400> SEQUENCE: 4 tagtctt 7

<210> SEQ ID NO 5
<211> LENGTH: 7
<212> TYPE: DNA
<213> ORGANISM: Artificial Sequence
<220> FEATURE:
<223> OTHER INFORMATION: made in laboratory

<400> SEQUENCE: 5 aagactg 7

<210> SEQ ID NO 6
<211> LENGTH: 7
<212> TYPE: DNA
<213> ORGANISM: Artificial Sequence
<220> FEATURE:
<223> OTHER INFORMATION: made in laboratory

<400> SEQUENCE: 6 cagtctt 7

<210> SEQ ID NO 7
<211> LENGTH: 7
<212> TYPE: DNA
<213> ORGANISM: Artificial Sequence
<220> FEATURE:
<223> OTHER INFORMATION: made in laboratory

<400> SEQUENCE: 7 aagactc 7

<210> SEQ ID NO 8
<211> LENGTH: 7
<212> TYPE: DNA
<213> ORGANISM: Artificial Sequence
<220> FEATURE:
<223> OTHER INFORMATION: made in laboratory

<400> SEQUENCE: 8 gagtctt 7

<210> SEQ ID NO 9
<211> LENGTH: 7
<212> TYPE: DNA
<213> ORGANISM: Artificial Sequence
<220> FEATURE:
<223> OTHER INFORMATION: made in laboratory

<400> SEQUENCE: 9 aagactt 7

<210> SEQ ID NO 10
<211> LENGTH: 7
<212> TYPE: DNA
<213> ORGANISM: Artificial Sequence
<220> FEATURE:
<223> OTHER INFORMATION: made in laboratory

<400> SEQUENCE: 10 aagtctt 7

<210> SEQ ID NO 11
<211> LENGTH: 7
<212> TYPE: DNA
<213> ORGANISM: Artificial Sequence
<220> FEATURE:
<223> OTHER INFORMATION: made in laboratory

<400> SEQUENCE: 11 aaggcta 7

<210> SEQ ID NO 12
<211> LENGTH: 7

<212> TYPE: DNA
<213> ORGANISM: Artificial Sequence
<220> FEATURE:
<223> OTHER INFORMATION: made in laboratory

<400> SEQUENCE: 12 tagcctt 7

<210> SEQ ID NO 13
<211> LENGTH: 7
<212> TYPE: DNA
<213> ORGANISM: Artificial Sequence
<220> FEATURE:
<223> OTHER INFORMATION: made in laboratory

<400> SEQUENCE: 13 aaggctg 7

<210> SEQ ID NO 14
<211> LENGTH: 7
<212> TYPE: DNA
<213> ORGANISM: Artificial Sequence
<220> FEATURE:
<223> OTHER INFORMATION: made in laboratory

<400> SEQUENCE: 14 cagcctt 7

<210> SEQ ID NO 15
<211> LENGTH: 7
<212> TYPE: DNA
<213> ORGANISM: Artificial Sequence
<220> FEATURE:
<223> OTHER INFORMATION: made in laboratory

<400> SEQUENCE: 15 aaggctc 7

<210> SEQ ID NO 16
<211> LENGTH: 7
<212> TYPE: DNA
<213> ORGANISM: Artificial Sequence
<220> FEATURE:
<223> OTHER INFORMATION: made in laboratory

<400> SEQUENCE: 16 gagcctt 7

<210> SEQ ID NO 17
<211> LENGTH: 7
<212> TYPE: DNA
<213> ORGANISM: Artificial Sequence
<220> FEATURE:
<223> OTHER INFORMATION: made in laboratory

<400> SEQUENCE: 17 aaggctt 7

<210> SEQ ID NO 18
<211> LENGTH: 7
<212> TYPE: DNA
<213> ORGANISM: Artificial Sequence
<220> FEATURE:
<223> OTHER INFORMATION: made in laboratory

<400> SEQUENCE: 18 aagcctt 7

<210> SEQ ID NO 19
<211> LENGTH: 7
<212> TYPE: DNA
<213> ORGANISM: Artificial Sequence
<220> FEATURE:
<223> OTHER INFORMATION: made in laboratory

<400> SEQUENCE: 19 aagccta 7

<210> SEQ ID NO 20
<211> LENGTH: 7
<212> TYPE: DNA
<213> ORGANISM: Artificial Sequence
<220> FEATURE:
<223> OTHER INFORMATION: made in laboratory

<400> SEQUENCE: 20 taggctt 7

<210> SEQ ID NO 21
<211> LENGTH: 7
<212> TYPE: DNA
<213> ORGANISM: Artificial Sequence
<220> FEATURE:
<223> OTHER INFORMATION: made in laboratory

<400> SEQUENCE: 21 aagcctg 7

<210> SEQ ID NO 22
<211> LENGTH: 7
<212> TYPE: DNA
<213> ORGANISM: Artificial Sequence
<220> FEATURE:
<223> OTHER INFORMATION: made in laboratory

<400> SEQUENCE: 22 caggctt 7

<210> SEQ ID NO 23
<211> LENGTH: 7
<212> TYPE: DNA
<213> ORGANISM: Artificial Sequence
<220> FEATURE:
<223> OTHER INFORMATION: made in laboratory

<400> SEQUENCE: 23 aagcctc 7

<210> SEQ ID NO 24
<211> LENGTH: 7
<212> TYPE: DNA
<213> ORGANISM: Artificial Sequence
<220> FEATURE:
<223> OTHER INFORMATION: made in laboratory

<400> SEQUENCE: 24 gaggctt 7

<210> SEQ ID NO 25
<211> LENGTH: 7
<212> TYPE: DNA
<213> ORGANISM: Artificial Sequence
<220> FEATURE:
<223> OTHER INFORMATION: made in laboratory

<400> SEQUENCE: 25 aagcctt 7

<210> SEQ ID NO 26
<211> LENGTH: 7
<212> TYPE: DNA
<213> ORGANISM: Artificial Sequence
<220> FEATURE:
<223> OTHER INFORMATION: made in laboratory

<400> SEQUENCE: 26 aaggctt 7

<210> SEQ ID NO 27
<211> LENGTH: 7
<212> TYPE: DNA
<213> ORGANISM: Artificial Sequence
<220> FEATURE:
<223> OTHER INFORMATION: made in laboratory

<400> SEQUENCE: 27 aagtcta 7

<210> SEQ ID NO 28
<211> LENGTH: 7
<212> TYPE: DNA
<213> ORGANISM: Artificial Sequence
<220> FEATURE:
<223> OTHER INFORMATION: made in laboratory

<400> SEQUENCE: 28 tagactt 7

<210> SEQ ID NO 29
<211> LENGTH: 7
<212> TYPE: DNA
<213> ORGANISM: Artificial Sequence
<220> FEATURE:
<223> OTHER INFORMATION: made in laboratory

<400> SEQUENCE: 29 aagtctg 7

<210> SEQ ID NO 30
<211> LENGTH: 7
<212> TYPE: DNA
<213> ORGANISM: Artificial Sequence
<220> FEATURE:
<223> OTHER INFORMATION: made in laboratory

<400> SEQUENCE: 30 cagactt 7

<210> SEQ ID NO 31
<211> LENGTH: 7
<212> TYPE: DNA
<213> ORGANISM: Artificial Sequence
<220> FEATURE:
<223> OTHER INFORMATION: made in laboratory

<400> SEQUENCE: 31 aagtctc 7

<210> SEQ ID NO 32
<211> LENGTH: 7
<212> TYPE: DNA
<213> ORGANISM: Artificial Sequence
<220> FEATURE:
<223> OTHER INFORMATION: made in laboratory

<400> SEQUENCE: 32 gagactt 7

<210> SEQ ID NO 33
<211> LENGTH: 7
<212> TYPE: DNA
<213> ORGANISM: Artificial Sequence
<220> FEATURE:
<223> OTHER INFORMATION: made in laboratory

<400> SEQUENCE: 33 aagtctt 7

<210> SEQ ID NO 34
<211> LENGTH: 7
<212> TYPE: DNA
<213> ORGANISM: Artificial Sequence
<220> FEATURE:
<223> OTHER INFORMATION: made in laboratory

<400> SEQUENCE: 34 aagactt 7

<210> SEQ ID NO 35
<211> LENGTH: 7
<212> TYPE: DNA
<213> ORGANISM: Artificial Sequence
<220> FEATURE:
<223> OTHER INFORMATION: made in laboratory

<400> SEQUENCE: 35 gagacta 7

<210> SEQ ID NO 36
<211> LENGTH: 7
<212> TYPE: DNA
<213> ORGANISM: Artificial Sequence
<220> FEATURE:
<223> OTHER INFORMATION: made in laboratory

<400> SEQUENCE: 36 tagtctc 7

<210> SEQ ID NO 37
<211> LENGTH: 7
<212> TYPE: DNA
<213> ORGANISM: Artificial Sequence
<220> FEATURE:
<223> OTHER INFORMATION: made in laboratory

<400> SEQUENCE: 37 gagactg 7

<210> SEQ ID NO 38
<211> LENGTH: 7
<212> TYPE: DNA
<213> ORGANISM: Artificial Sequence
<220> FEATURE:
<223> OTHER INFORMATION: made in laboratory

<400> SEQUENCE: 38 cagtctc 7

<210> SEQ ID NO 39
<211> LENGTH: 7
<212> TYPE: DNA
<213> ORGANISM: Artificial Sequence
<220> FEATURE:
<223> OTHER INFORMATION: made in laboratory

<400> SEQUENCE: 39 gagactc 7

<210> SEQ ID NO 40
<211> LENGTH: 7
<212> TYPE: DNA
<213> ORGANISM: Artificial Sequence
<220> FEATURE:
<223> OTHER INFORMATION: made in laboratory

<400> SEQUENCE: 40 gagactc 7

<210> SEQ ID NO 41
<211> LENGTH: 7
<212> TYPE: DNA
<213> ORGANISM: Artificial Sequence
<220> FEATURE:
<223> OTHER INFORMATION: made in laboratory

<400> SEQUENCE: 41 gagactc 7

<210> SEQ ID NO 42
<211> LENGTH: 7
<212> TYPE: DNA
<213> ORGANISM: Artificial Sequence
<220> FEATURE:
<223> OTHER INFORMATION: made in laboratory

<400> SEQUENCE: 42 aagtctc 7

<210> SEQ ID NO 43
<211> LENGTH: 7
<212> TYPE: DNA
<213> ORGANISM: Artificial Sequence
<220> FEATURE:
<223> OTHER INFORMATION: made in laboratory

<400> SEQUENCE: 43 gaggcta 7

<210> SEQ ID NO 44
<211> LENGTH: 7
<212> TYPE: DNA
<213> ORGANISM: Artificial Sequence
<220> FEATURE:
<223> OTHER INFORMATION: made in laboratory

<400> SEQUENCE: 44 tagcctc 7

<210> SEQ ID NO 45

<211> LENGTH: 7
<212> TYPE: DNA
<213> ORGANISM: Artificial Sequence
<220> FEATURE:
<223> OTHER INFORMATION: made in laboratory

<400> SEQUENCE: 45 gaggctg 7

<210> SEQ ID NO 46
<211> LENGTH: 7
<212> TYPE: DNA
<213> ORGANISM: Artificial Sequence
<220> FEATURE:
<223> OTHER INFORMATION: made in laboratory

<400> SEQUENCE: 46 cagcctc 7

<210> SEQ ID NO 47
<211> LENGTH: 7
<212> TYPE: DNA
<213> ORGANISM: Artificial Sequence
<220> FEATURE:
<223> OTHER INFORMATION: made in laboratory

<400> SEQUENCE: 47 gaggctc 7

<210> SEQ ID NO 48
<211> LENGTH: 7
<212> TYPE: DNA
<213> ORGANISM: Artificial Sequence
<220> FEATURE:
<223> OTHER INFORMATION: made in laboratory

<400> SEQUENCE: 48 gagcctc 7

<210> SEQ ID NO 49
<211> LENGTH: 7
<212> TYPE: DNA
<213> ORGANISM: Artificial Sequence
<220> FEATURE:
<223> OTHER INFORMATION: made in laboratory

<400> SEQUENCE: 49 gaggctt 7

<210> SEQ ID NO 50
<211> LENGTH: 7
<212> TYPE: DNA
<213> ORGANISM: Artificial Sequence
<220> FEATURE:
<223> OTHER INFORMATION: made in laboratory

<400> SEQUENCE: 50 aagcctc 7

<210> SEQ ID NO 51
<211> LENGTH: 7
<212> TYPE: DNA
<213> ORGANISM: Artificial Sequence
<220> FEATURE:
<223> OTHER INFORMATION: made in laboratory

<400> SEQUENCE: 51 gagccta 7

<210> SEQ ID NO 52
<211> LENGTH: 7
<212> TYPE: DNA
<213> ORGANISM: Artificial Sequence
<220> FEATURE:
<223> OTHER INFORMATION: made in laboratory

<400> SEQUENCE: 52 taggctc 7

<210> SEQ ID NO 53
<211> LENGTH: 7
<212> TYPE: DNA
<213> ORGANISM: Artificial Sequence
<220> FEATURE:
<223> OTHER INFORMATION: made in laboratory

<400> SEQUENCE: 53 gagcctg 7

<210> SEQ ID NO 54
<211> LENGTH: 7
<212> TYPE: DNA
<213> ORGANISM: Artificial Sequence
<220> FEATURE:
<223> OTHER INFORMATION: made in laboratory

<400> SEQUENCE: 54 caggctc 7

<210> SEQ ID NO 55
<211> LENGTH: 7
<212> TYPE: DNA
<213> ORGANISM: Artificial Sequence
<220> FEATURE:
<223> OTHER INFORMATION: made in laboratory

<400> SEQUENCE: 55 gagcctc 7

<210> SEQ ID NO 56
<211> LENGTH: 7
<212> TYPE: DNA
<213> ORGANISM: Artificial Sequence
<220> FEATURE:
<223> OTHER INFORMATION: made in laboratory

<400> SEQUENCE: 56 gaggctc 7

<210> SEQ ID NO 57
<211> LENGTH: 7
<212> TYPE: DNA
<213> ORGANISM: Artificial Sequence
<220> FEATURE:
<223> OTHER INFORMATION: made in laboratory

<400> SEQUENCE: 57 gagcctt 7

<210> SEQ ID NO 58
<211> LENGTH: 7
<212> TYPE: DNA

<213> ORGANISM: Artificial Sequence
<220> FEATURE:
<223> OTHER INFORMATION: made in laboratory

<400> SEQUENCE: 58 aaggctc 7

<210> SEQ ID NO 59
<211> LENGTH: 7
<212> TYPE: DNA
<213> ORGANISM: Artificial Sequence
<220> FEATURE:
<223> OTHER INFORMATION: made in laboratory

<400> SEQUENCE: 59 gagtcta 7

<210> SEQ ID NO 60
<211> LENGTH: 7
<212> TYPE: DNA
<213> ORGANISM: Artificial Sequence
<220> FEATURE:
<223> OTHER INFORMATION: made in laboratory

<400> SEQUENCE: 60 tagactc 7

<210> SEQ ID NO 61
<211> LENGTH: 7
<212> TYPE: DNA
<213> ORGANISM: Artificial Sequence
<220> FEATURE:
<223> OTHER INFORMATION: made in laboratory

<400> SEQUENCE: 61 gagtctg 7

<210> SEQ ID NO 62
<211> LENGTH: 7
<212> TYPE: DNA
<213> ORGANISM: Artificial Sequence
<220> FEATURE:
<223> OTHER INFORMATION: made in laboratory

<400> SEQUENCE: 62 cagactc 7

<210> SEQ ID NO 63
<211> LENGTH: 7
<212> TYPE: DNA
<213> ORGANISM: Artificial Sequence
<220> FEATURE:
<223> OTHER INFORMATION: made in laboratory

<400> SEQUENCE: 63 gagtctc 7

<210> SEQ ID NO 64
<211> LENGTH: 7
<212> TYPE: DNA
<213> ORGANISM: Artificial Sequence
<220> FEATURE:
<223> OTHER INFORMATION: made in laboratory

<400> SEQUENCE: 64 gagactc 7

<210> SEQ ID NO 65
<211> LENGTH: 7
<212> TYPE: DNA
<213> ORGANISM: Artificial Sequence
<220> FEATURE:
<223> OTHER INFORMATION: made in laboratory

<400> SEQUENCE: 65 gagtctt 7

<210> SEQ ID NO 66
<211> LENGTH: 7
<212> TYPE: DNA
<213> ORGANISM: Artificial Sequence
<220> FEATURE:
<223> OTHER INFORMATION: made in laboratory

<400> SEQUENCE: 66 aagactc 7

<210> SEQ ID NO 67
<211> LENGTH: 7
<212> TYPE: DNA
<213> ORGANISM: Artificial Sequence
<220> FEATURE:
<223> OTHER INFORMATION: made in laboratory

<400> SEQUENCE: 67 cagacta 7

<210> SEQ ID NO 68
<211> LENGTH: 7
<212> TYPE: DNA
<213> ORGANISM: Artificial Sequence
<220> FEATURE:
<223> OTHER INFORMATION: made in laboratory

<400> SEQUENCE: 68 tagtctg 7

<210> SEQ ID NO 69
<211> LENGTH: 7
<212> TYPE: DNA
<213> ORGANISM: Artificial Sequence
<220> FEATURE:
<223> OTHER INFORMATION: made in laboratory

<400> SEQUENCE: 69 cagactg 7

<210> SEQ ID NO 70
<211> LENGTH: 7
<212> TYPE: DNA
<213> ORGANISM: Artificial Sequence
<220> FEATURE:
<223> OTHER INFORMATION: made in laboratory

<400> SEQUENCE: 70 cagtctg 7

<210> SEQ ID NO 71
<211> LENGTH: 7
<212> TYPE: DNA
<213> ORGANISM: Artificial Sequence
<220> FEATURE:

<223> OTHER INFORMATION: made in laboratory

<400> SEQUENCE: 71 cagactc 7

<210> SEQ ID NO 72
<211> LENGTH: 7
<212> TYPE: DNA
<213> ORGANISM: Artificial Sequence
<220> FEATURE:
<223> OTHER INFORMATION: made in laboratory

<400> SEQUENCE: 72 gagtctg 7

<210> SEQ ID NO 73
<211> LENGTH: 7
<212> TYPE: DNA
<213> ORGANISM: Artificial Sequence
<220> FEATURE:
<223> OTHER INFORMATION: made in laboratory

<400> SEQUENCE: 73 cagactt 7

<210> SEQ ID NO 74
<211> LENGTH: 7
<212> TYPE: DNA
<213> ORGANISM: Artificial Sequence
<220> FEATURE:
<223> OTHER INFORMATION: made in laboratory

<400> SEQUENCE: 74 aagtctg 7

<210> SEQ ID NO 75
<211> LENGTH: 7
<212> TYPE: DNA
<213> ORGANISM: Artificial Sequence
<220> FEATURE:
<223> OTHER INFORMATION: made in laboratory

<400> SEQUENCE: 75 caggcta 7

<210> SEQ ID NO 76
<211> LENGTH: 7
<212> TYPE: DNA
<213> ORGANISM: Artificial Sequence
<220> FEATURE:
<223> OTHER INFORMATION: made in laboratory

<400> SEQUENCE: 76 tagcctg 7

<210> SEQ ID NO 77
<211> LENGTH: 7
<212> TYPE: DNA
<213> ORGANISM: Artificial Sequence
<220> FEATURE:
<223> OTHER INFORMATION: made in laboratory

<400> SEQUENCE: 77 caggctg 7

<210> SEQ ID NO 78
<211> LENGTH: 7
<212> TYPE: DNA
<213> ORGANISM: Artificial Sequence
<220> FEATURE:
<223> OTHER INFORMATION: made in laboratory

<400> SEQUENCE: 78 cagcctg 7

<210> SEQ ID NO 79
<211> LENGTH: 7
<212> TYPE: DNA
<213> ORGANISM: Artificial Sequence
<220> FEATURE:
<223> OTHER INFORMATION: made in laboratory

<400> SEQUENCE: 79 caggctc 7

<210> SEQ ID NO 80
<211> LENGTH: 7
<212> TYPE: DNA
<213> ORGANISM: Artificial Sequence
<220> FEATURE:
<223> OTHER INFORMATION: made in laboratory

<400> SEQUENCE: 80 gagcctg 7

<210> SEQ ID NO 81
<211> LENGTH: 7
<212> TYPE: DNA
<213> ORGANISM: Artificial Sequence
<220> FEATURE:
<223> OTHER INFORMATION: made in laboratory

<400> SEQUENCE: 81 caggctt 7

<210> SEQ ID NO 82
<211> LENGTH: 7
<212> TYPE: DNA
<213> ORGANISM: Artificial Sequence
<220> FEATURE:
<223> OTHER INFORMATION: made in laboratory

<400> SEQUENCE: 82 aagcctg 7

<210> SEQ ID NO 83
<211> LENGTH: 7
<212> TYPE: DNA
<213> ORGANISM: Artificial Sequence
<220> FEATURE:
<223> OTHER INFORMATION: made in laboratory

<400> SEQUENCE: 83 cagccta 7

<210> SEQ ID NO 84
<211> LENGTH: 7
<212> TYPE: DNA
<213> ORGANISM: Artificial Sequence
<220> FEATURE:
<223> OTHER INFORMATION: made in laboratory

<400> SEQUENCE: 84 taggctg 7

<210> SEQ ID NO 85
<211> LENGTH: 7
<212> TYPE: DNA
<213> ORGANISM: Artificial Sequence
<220> FEATURE:
<223> OTHER INFORMATION: made in laboratory

<400> SEQUENCE: 85 cagcctg 7

<210> SEQ ID NO 86
<211> LENGTH: 7
<212> TYPE: DNA
<213> ORGANISM: Artificial Sequence
<220> FEATURE:
<223> OTHER INFORMATION: made in laboratory

<400> SEQUENCE: 86 caggctg 7

<210> SEQ ID NO 87
<211> LENGTH: 7
<212> TYPE: DNA
<213> ORGANISM: Artificial Sequence
<220> FEATURE:
<223> OTHER INFORMATION: made in laboratory

<400> SEQUENCE: 87 caggctg 7

<210> SEQ ID NO 88
<211> LENGTH: 7
<212> TYPE: DNA
<213> ORGANISM: Artificial Sequence
<220> FEATURE:
<223> OTHER INFORMATION: made in laboratory

<400> SEQUENCE: 88 gaggctg 7

<210> SEQ ID NO 89
<211> LENGTH: 7
<212> TYPE: DNA
<213> ORGANISM: Artificial Sequence
<220> FEATURE:
<223> OTHER INFORMATION: made in laboratory

<400> SEQUENCE: 89 cagcctt 7

<210> SEQ ID NO 90
<211> LENGTH: 7
<212> TYPE: DNA
<213> ORGANISM: Artificial Sequence
<220> FEATURE:
<223> OTHER INFORMATION: made in laboratory

<400> SEQUENCE: 90 aaggctg 7

<210> SEQ ID NO 91
<211> LENGTH: 7

<212> TYPE: DNA
<213> ORGANISM: Artificial Sequence
<220> FEATURE:
<223> OTHER INFORMATION: made in laboratory

<400> SEQUENCE: 91 cagtcta 7

<210> SEQ ID NO 92
<211> LENGTH: 7
<212> TYPE: DNA
<213> ORGANISM: Artificial Sequence
<220> FEATURE:
<223> OTHER INFORMATION: made in laboratory

<400> SEQUENCE: 92 tagactg 7

<210> SEQ ID NO 93
<211> LENGTH: 7
<212> TYPE: DNA
<213> ORGANISM: Artificial Sequence
<220> FEATURE:
<223> OTHER INFORMATION: made in laboratory

<400> SEQUENCE: 93 cagtctg 7

<210> SEQ ID NO 94
<211> LENGTH: 7
<212> TYPE: DNA
<213> ORGANISM: Artificial Sequence
<220> FEATURE:
<223> OTHER INFORMATION: made in laboratory

<400> SEQUENCE: 94 cagactg 7

<210> SEQ ID NO 95
<211> LENGTH: 7
<212> TYPE: DNA
<213> ORGANISM: Artificial Sequence
<220> FEATURE:
<223> OTHER INFORMATION: made in laboratory

<400> SEQUENCE: 95 cagtctc 7

<210> SEQ ID NO 96
<211> LENGTH: 7
<212> TYPE: DNA
<213> ORGANISM: Artificial Sequence
<220> FEATURE:
<223> OTHER INFORMATION: made in laboratory

<400> SEQUENCE: 96 gagactg 7

<210> SEQ ID NO 97
<211> LENGTH: 7
<212> TYPE: DNA
<213> ORGANISM: Artificial Sequence
<220> FEATURE:
<223> OTHER INFORMATION: made in laboratory

<400> SEQUENCE: 97 cagtctt 7

<210> SEQ ID NO 98
<211> LENGTH: 7
<212> TYPE: DNA
<213> ORGANISM: Artificial Sequence
<220> FEATURE:
<223> OTHER INFORMATION: made in laboratory

<400> SEQUENCE: 98 aagactg 7

<210> SEQ ID NO 99
<211> LENGTH: 7
<212> TYPE: DNA
<213> ORGANISM: Artificial Sequence
<220> FEATURE:
<223> OTHER INFORMATION: made in laboratory

<400> SEQUENCE: 99 tagacta 7

<210> SEQ ID NO 100
<211> LENGTH: 7
<212> TYPE: DNA
<213> ORGANISM: Artificial Sequence
<220> FEATURE:
<223> OTHER INFORMATION: made in laboratory

<400> SEQUENCE: 100 tagtcta 7

<210> SEQ ID NO 101
<211> LENGTH: 7
<212> TYPE: DNA
<213> ORGANISM: Artificial Sequence
<220> FEATURE:
<223> OTHER INFORMATION: made in laboratory

<400> SEQUENCE: 101 tagactg 7

<210> SEQ ID NO 102
<211> LENGTH: 7
<212> TYPE: DNA
<213> ORGANISM: Artificial Sequence
<220> FEATURE:
<223> OTHER INFORMATION: made in laboratory

<400> SEQUENCE: 102 cagtcta 7

<210> SEQ ID NO 103
<211> LENGTH: 7
<212> TYPE: DNA
<213> ORGANISM: Artificial Sequence
<220> FEATURE:
<223> OTHER INFORMATION: made in laboratory

<400> SEQUENCE: 103 tagactc 7

<210> SEQ ID NO 104
<211> LENGTH: 7
<212> TYPE: DNA
<213> ORGANISM: Artificial Sequence
<220> FEATURE:
<223> OTHER INFORMATION: made in laboratory

<400> SEQUENCE: 104 gagtcta 7

<210> SEQ ID NO 105
<211> LENGTH: 7
<212> TYPE: DNA
<213> ORGANISM: Artificial Sequence
<220> FEATURE:
<223> OTHER INFORMATION: made in laboratory

<400> SEQUENCE: 105 tagactt 7

<210> SEQ ID NO 106
<211> LENGTH: 7
<212> TYPE: DNA
<213> ORGANISM: Artificial Sequence
<220> FEATURE:
<223> OTHER INFORMATION: made in laboratory

<400> SEQUENCE: 106 aagtcta 7

<210> SEQ ID NO 107
<211> LENGTH: 7
<212> TYPE: DNA
<213> ORGANISM: Artificial Sequence
<220> FEATURE:
<223> OTHER INFORMATION: made in laboratory

<400> SEQUENCE: 107 taggcta 7

<210> SEQ ID NO 108
<211> LENGTH: 7
<212> TYPE: DNA
<213> ORGANISM: Artificial Sequence
<220> FEATURE:
<223> OTHER INFORMATION: made in laboratory

<400> SEQUENCE: 108 tagccta 7

<210> SEQ ID NO 109
<211> LENGTH: 7
<212> TYPE: DNA
<213> ORGANISM: Artificial Sequence
<220> FEATURE:
<223> OTHER INFORMATION: made in laboratory

<400> SEQUENCE: 109 taggctg 7

<210> SEQ ID NO 110
<211> LENGTH: 7
<212> TYPE: DNA
<213> ORGANISM: Artificial Sequence
<220> FEATURE:
<223> OTHER INFORMATION: made in laboratory

<400> SEQUENCE: 110 cagccta 7

<210> SEQ ID NO 111
<211> LENGTH: 7
<212> TYPE: DNA
<213> ORGANISM: Artificial Sequence
<220> FEATURE:
<223> OTHER INFORMATION: made in laboratory

<400> SEQUENCE: 111 taggctc 7

<210> SEQ ID NO 112
<211> LENGTH: 7
<212> TYPE: DNA
<213> ORGANISM: Artificial Sequence
<220> FEATURE:
<223> OTHER INFORMATION: made in laboratory

<400> SEQUENCE: 112 gagccta 7

<210> SEQ ID NO 113
<211> LENGTH: 7
<212> TYPE: DNA
<213> ORGANISM: Artificial Sequence
<220> FEATURE:
<223> OTHER INFORMATION: made in laboratory

<400> SEQUENCE: 113 taggctt 7

<210> SEQ ID NO 114
<211> LENGTH: 7
<212> TYPE: DNA
<213> ORGANISM: Artificial Sequence
<220> FEATURE:
<223> OTHER INFORMATION: made in laboratory

<400> SEQUENCE: 114 aagccta 7

<210> SEQ ID NO 115
<211> LENGTH: 7
<212> TYPE: DNA
<213> ORGANISM: Artificial Sequence
<220> FEATURE:
<223> OTHER INFORMATION: made in laboratory

<400> SEQUENCE: 115 tagccta 7

<210> SEQ ID NO 116
<211> LENGTH: 7
<212> TYPE: DNA
<213> ORGANISM: Artificial Sequence
<220> FEATURE:
<223> OTHER INFORMATION: made in laboratory

<400> SEQUENCE: 116 taggcta 7

<210> SEQ ID NO 117
<211> LENGTH: 7
<212> TYPE: DNA
<213> ORGANISM: Artificial Sequence
<220> FEATURE:
<223> OTHER INFORMATION: made in laboratory

<400> SEQUENCE: 117 tagcctg 7

<210> SEQ ID NO 118
<211> LENGTH: 7
<212> TYPE: DNA
<213> ORGANISM: Artificial Sequence
<220> FEATURE:
<223> OTHER INFORMATION: made in laboratory

<400> SEQUENCE: 118 caggcta 7

<210> SEQ ID NO 119
<211> LENGTH: 7
<212> TYPE: DNA
<213> ORGANISM: Artificial Sequence
<220> FEATURE:
<223> OTHER INFORMATION: made in laboratory

<400> SEQUENCE: 119 tagcctc 7

<210> SEQ ID NO 120
<211> LENGTH: 7
<212> TYPE: DNA
<213> ORGANISM: Artificial Sequence
<220> FEATURE:
<223> OTHER INFORMATION: made in laboratory

<400> SEQUENCE: 120 gaggcta 7

<210> SEQ ID NO 121
<211> LENGTH: 7
<212> TYPE: DNA
<213> ORGANISM: Artificial Sequence
<220> FEATURE:
<223> OTHER INFORMATION: made in laboratory

<400> SEQUENCE: 121 tagcctt 7

<210> SEQ ID NO 122
<211> LENGTH: 7
<212> TYPE: DNA
<213> ORGANISM: Artificial Sequence
<220> FEATURE:
<223> OTHER INFORMATION: made in laboratory

<400> SEQUENCE: 122 aaggcta 7

<210> SEQ ID NO 123
<211> LENGTH: 7
<212> TYPE: DNA
<213> ORGANISM: Artificial Sequence
<220> FEATURE:
<223> OTHER INFORMATION: made in laboratory

<400> SEQUENCE: 123 tagtcta 7

<210> SEQ ID NO 124

<211> LENGTH: 7
<212> TYPE: DNA
<213> ORGANISM: Artificial Sequence
<220> FEATURE:
<223> OTHER INFORMATION: made in laboratory

<400> SEQUENCE: 124 tagacta 7

<210> SEQ ID NO 125
<211> LENGTH: 7
<212> TYPE: DNA
<213> ORGANISM: Artificial Sequence
<220> FEATURE:
<223> OTHER INFORMATION: made in laboratory

<400> SEQUENCE: 125 tagtctg 7

<210> SEQ ID NO 126
<211> LENGTH: 7
<212> TYPE: DNA
<213> ORGANISM: Artificial Sequence
<220> FEATURE:
<223> OTHER INFORMATION: made in laboratory

<400> SEQUENCE: 126 cagacta 7

<210> SEQ ID NO 127
<211> LENGTH: 7
<212> TYPE: DNA
<213> ORGANISM: Artificial Sequence
<220> FEATURE:
<223> OTHER INFORMATION: made in laboratory

<400> SEQUENCE: 127 tagtctc 7

<210> SEQ ID NO 128
<211> LENGTH: 7
<212> TYPE: DNA
<213> ORGANISM: Artificial Sequence
<220> FEATURE:
<223> OTHER INFORMATION: made in laboratory

<400> SEQUENCE: 128 gagacta 7

<210> SEQ ID NO 129
<211> LENGTH: 7
<212> TYPE: DNA
<213> ORGANISM: Artificial Sequence
<220> FEATURE:
<223> OTHER INFORMATION: made in laboratory

<400> SEQUENCE: 129 tagtctt 7

<210> SEQ ID NO 130
<211> LENGTH: 7
<212> TYPE: DNA
<213> ORGANISM: Artificial Sequence
<220> FEATURE:
<223> OTHER INFORMATION: made in laboratory

<400> SEQUENCE: 130 aagacta 7

<210> SEQ ID NO 131
<211> LENGTH: 74
<212> TYPE: DNA
<213> ORGANISM: Artificial Sequence
<220> FEATURE:
<223> OTHER INFORMATION: made in laboratory
<220> FEATURE:
<221> NAME/KEY: misc_feature
<222> LOCATION: (26)..(33)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t

<400> SEQUENCE: 131
aatgatacgg cgaccaccga gatctnnnnn nnnacactct ttccctacac gacgctcttc 60
cgatcnagcn tagn 74

<210> SEQ ID NO 132
<211> LENGTH: 73
<212> TYPE: DNA
<213> ORGANISM: Artificial Sequence
<220> FEATURE:
<223> OTHER INFORMATION: made in laboratory
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (43)..(50)
<223> OTHER INFORMATION: n is a, c, g, or t

<400> SEQUENCE: 132
nctangctng atcggaagag cacacgtctg aactccagtc acnnnnnnnn atctcgtatg 60
ccgtcttctg ctt 73

<210> SEQ ID NO 133
<211> LENGTH: 9
<212> TYPE: DNA
<213> ORGANISM: Artificial Sequence
<220> FEATURE:
<223> OTHER INFORMATION: made in laboratory

<400> SEQUENCE: 133 aagcataga 9

<210> SEQ ID NO 134
<211> LENGTH: 9
<212> TYPE: DNA

<213> ORGANISM: Artificial Sequence
<220> FEATURE:
<223> OTHER INFORMATION: made in laboratory

<400> SEQUENCE: 134 tagcttagt 9

<210> SEQ ID NO 135
<211> LENGTH: 9
<212> TYPE: DNA
<213> ORGANISM: Artificial Sequence
<220> FEATURE:
<223> OTHER INFORMATION: made in laboratory

<400> SEQUENCE: 135 aagcatagg 9

<210> SEQ ID NO 136
<211> LENGTH: 9
<212> TYPE: DNA
<213> ORGANISM: Artificial Sequence
<220> FEATURE:
<223> OTHER INFORMATION: made in laboratory

<400> SEQUENCE: 136 cagcttagt 9

<210> SEQ ID NO 137
<211> LENGTH: 9
<212> TYPE: DNA
<213> ORGANISM: Artificial Sequence
<220> FEATURE:
<223> OTHER INFORMATION: made in laboratory

<400> SEQUENCE: 137 aagcatagc 9

<210> SEQ ID NO 138
<211> LENGTH: 9
<212> TYPE: DNA
<213> ORGANISM: Artificial Sequence
<220> FEATURE:
<223> OTHER INFORMATION: made in laboratory

<400> SEQUENCE: 138 gagcttagt 9

<210> SEQ ID NO 139
<211> LENGTH: 9
<212> TYPE: DNA
<213> ORGANISM: Artificial Sequence
<220> FEATURE:
<223> OTHER INFORMATION: made in laboratory

<400> SEQUENCE: 139 aagcatagt 9

<210> SEQ ID NO 140
<211> LENGTH: 9
<212> TYPE: DNA
<213> ORGANISM: Artificial Sequence
<220> FEATURE:
<223> OTHER INFORMATION: made in laboratory

<400> SEQUENCE: 140 aagcttagt 9

<210> SEQ ID NO 141
<211> LENGTH: 9
<212> TYPE: DNA
<213> ORGANISM: Artificial Sequence
<220> FEATURE:
<223> OTHER INFORMATION: made in laboratory

<400> SEQUENCE: 141 aagcgtaga 9

<210> SEQ ID NO 142
<211> LENGTH: 9
<212> TYPE: DNA
<213> ORGANISM: Artificial Sequence
<220> FEATURE:
<223> OTHER INFORMATION: made in laboratory

<400> SEQUENCE: 142 tagcctagt 9

<210> SEQ ID NO 143
<211> LENGTH: 9
<212> TYPE: DNA
<213> ORGANISM: Artificial Sequence
<220> FEATURE:
<223> OTHER INFORMATION: made in laboratory

<400> SEQUENCE: 143 aagcgtagg 9

<210> SEQ ID NO 144
<211> LENGTH: 9
<212> TYPE: DNA
<213> ORGANISM: Artificial Sequence
<220> FEATURE:
<223> OTHER INFORMATION: made in laboratory

<400> SEQUENCE: 144 cagcctagt 9

<210> SEQ ID NO 145
<211> LENGTH: 9
<212> TYPE: DNA
<213> ORGANISM: Artificial Sequence
<220> FEATURE:
<223> OTHER INFORMATION: made in laboratory

<400> SEQUENCE: 145 aagcgtagc 9

<210> SEQ ID NO 146
<211> LENGTH: 9
<212> TYPE: DNA
<213> ORGANISM: Artificial Sequence
<220> FEATURE:
<223> OTHER INFORMATION: made in laboratory

<400> SEQUENCE: 146 gagcctagt 9

<210> SEQ ID NO 147
<211> LENGTH: 9
<212> TYPE: DNA
<213> ORGANISM: Artificial Sequence
<220> FEATURE:

<223> OTHER INFORMATION: made in laboratory

<400> SEQUENCE: 147 aagcgtagt 9

<210> SEQ ID NO 148
<211> LENGTH: 9
<212> TYPE: DNA
<213> ORGANISM: Artificial Sequence
<220> FEATURE:
<223> OTHER INFORMATION: made in laboratory

<400> SEQUENCE: 148 aagcctagt 9

<210> SEQ ID NO 149
<211> LENGTH: 9
<212> TYPE: DNA
<213> ORGANISM: Artificial Sequence
<220> FEATURE:
<223> OTHER INFORMATION: made in laboratory

<400> SEQUENCE: 149 aagcctaga 9

<210> SEQ ID NO 150
<211> LENGTH: 9
<212> TYPE: DNA
<213> ORGANISM: Artificial Sequence
<220> FEATURE:
<223> OTHER INFORMATION: made in laboratory

<400> SEQUENCE: 150 tagcgtagt 9

<210> SEQ ID NO 151
<211> LENGTH: 9
<212> TYPE: DNA
<213> ORGANISM: Artificial Sequence
<220> FEATURE:
<223> OTHER INFORMATION: made in laboratory

<400> SEQUENCE: 151 aagcctagg 9

<210> SEQ ID NO 152
<211> LENGTH: 9
<212> TYPE: DNA
<213> ORGANISM: Artificial Sequence
<220> FEATURE:
<223> OTHER INFORMATION: made in laboratory

<400> SEQUENCE: 152 cagcgtagt 9

<210> SEQ ID NO 153
<211> LENGTH: 9
<212> TYPE: DNA
<213> ORGANISM: Artificial Sequence
<220> FEATURE:
<223> OTHER INFORMATION: made in laboratory

<400> SEQUENCE: 153 aagcctagc 9

<210> SEQ ID NO 154
<211> LENGTH: 9
<212> TYPE: DNA
<213> ORGANISM: Artificial Sequence
<220> FEATURE:
<223> OTHER INFORMATION: made in laboratory

<400> SEQUENCE: 154 gagcgtagt 9

<210> SEQ ID NO 155
<211> LENGTH: 9
<212> TYPE: DNA
<213> ORGANISM: Artificial Sequence
<220> FEATURE:
<223> OTHER INFORMATION: made in laboratory

<400> SEQUENCE: 155 aagcctagt 9

<210> SEQ ID NO 156
<211> LENGTH: 9
<212> TYPE: DNA
<213> ORGANISM: Artificial Sequence
<220> FEATURE:
<223> OTHER INFORMATION: made in laboratory

<400> SEQUENCE: 156 aagcgtagt 9

<210> SEQ ID NO 157
<211> LENGTH: 9
<212> TYPE: DNA
<213> ORGANISM: Artificial Sequence
<220> FEATURE:
<223> OTHER INFORMATION: made in laboratory

<400> SEQUENCE: 157 aagcttaga 9

<210> SEQ ID NO 158
<211> LENGTH: 9
<212> TYPE: DNA
<213> ORGANISM: Artificial Sequence
<220> FEATURE:
<223> OTHER INFORMATION: made in laboratory

<400> SEQUENCE: 158 tagcatagt 9

<210> SEQ ID NO 159
<211> LENGTH: 9
<212> TYPE: DNA
<213> ORGANISM: Artificial Sequence
<220> FEATURE:
<223> OTHER INFORMATION: made in laboratory

<400> SEQUENCE: 159 aagcttagg 9

<210> SEQ ID NO 160
<211> LENGTH: 9
<212> TYPE: DNA
<213> ORGANISM: Artificial Sequence
<220> FEATURE:
<223> OTHER INFORMATION: made in laboratory

<400> SEQUENCE: 160 cagcatagt 9

<210> SEQ ID NO 161
<211> LENGTH: 9
<212> TYPE: DNA
<213> ORGANISM: Artificial Sequence
<220> FEATURE:
<223> OTHER INFORMATION: made in laboratory

<400> SEQUENCE: 161 aagcttagc 9

<210> SEQ ID NO 162
<211> LENGTH: 9
<212> TYPE: DNA
<213> ORGANISM: Artificial Sequence
<220> FEATURE:
<223> OTHER INFORMATION: made in laboratory

<400> SEQUENCE: 162 gagcatagt 9

<210> SEQ ID NO 163
<211> LENGTH: 9
<212> TYPE: DNA
<213> ORGANISM: Artificial Sequence
<220> FEATURE:
<223> OTHER INFORMATION: made in laboratory

<400> SEQUENCE: 163 aagcttagt 9

<210> SEQ ID NO 164
<211> LENGTH: 9
<212> TYPE: DNA
<213> ORGANISM: Artificial Sequence
<220> FEATURE:
<223> OTHER INFORMATION: made in laboratory

<400> SEQUENCE: 164 aagcatagt 9

<210> SEQ ID NO 165
<211> LENGTH: 9
<212> TYPE: DNA
<213> ORGANISM: Artificial Sequence
<220> FEATURE:
<223> OTHER INFORMATION: made in laboratory

<400> SEQUENCE: 165 gagcataga 9

<210> SEQ ID NO 166
<211> LENGTH: 9
<212> TYPE: DNA
<213> ORGANISM: Artificial Sequence
<220> FEATURE:
<223> OTHER INFORMATION: made in laboratory

<400> SEQUENCE: 166 tagcttagc 9

<210> SEQ ID NO 167
<211> LENGTH: 9

<212> TYPE: DNA
<213> ORGANISM: Artificial Sequence
<220> FEATURE:
<223> OTHER INFORMATION: made in laboratory

<400> SEQUENCE: 167 gagcatagg 9

<210> SEQ ID NO 168
<211> LENGTH: 9
<212> TYPE: DNA
<213> ORGANISM: Artificial Sequence
<220> FEATURE:
<223> OTHER INFORMATION: made in laboratory

<400> SEQUENCE: 168 cagcttagc 9

<210> SEQ ID NO 169
<211> LENGTH: 9
<212> TYPE: DNA
<213> ORGANISM: Artificial Sequence
<220> FEATURE:
<223> OTHER INFORMATION: made in laboratory

<400> SEQUENCE: 169 gagcatagc 9

<210> SEQ ID NO 170
<211> LENGTH: 9
<212> TYPE: DNA
<213> ORGANISM: Artificial Sequence
<220> FEATURE:
<223> OTHER INFORMATION: made in laboratory

<400> SEQUENCE: 170 gagcttagc 9

<210> SEQ ID NO 171
<211> LENGTH: 9
<212> TYPE: DNA
<213> ORGANISM: Artificial Sequence
<220> FEATURE:
<223> OTHER INFORMATION: made in laboratory

<400> SEQUENCE: 171 gagcatagt 9

<210> SEQ ID NO 172
<211> LENGTH: 9
<212> TYPE: DNA
<213> ORGANISM: Artificial Sequence
<220> FEATURE:
<223> OTHER INFORMATION: made in laboratory

<400> SEQUENCE: 172 aagcttagc 9

<210> SEQ ID NO 173
<211> LENGTH: 9
<212> TYPE: DNA
<213> ORGANISM: Artificial Sequence
<220> FEATURE:
<223> OTHER INFORMATION: made in laboratory

<400> SEQUENCE: 173

```
gagcgtaga                                                          9


<210> SEQ ID NO 174
<211> LENGTH: 9
<212> TYPE: DNA
<213> ORGANISM: Artificial Sequence
<220> FEATURE:
<223> OTHER INFORMATION: made in laboratory

<400> SEQUENCE: 174

tagcctagc                                                          9


<210> SEQ ID NO 175
<211> LENGTH: 9
<212> TYPE: DNA
<213> ORGANISM: Artificial Sequence
<220> FEATURE:
<223> OTHER INFORMATION: made in laboratory

<400> SEQUENCE: 175

gagcgtagg                                                          9


<210> SEQ ID NO 176
<211> LENGTH: 9
<212> TYPE: DNA
<213> ORGANISM: Artificial Sequence
<220> FEATURE:
<223> OTHER INFORMATION: made in laboratory

<400> SEQUENCE: 176

cagcctagc                                                          9


<210> SEQ ID NO 177
<211> LENGTH: 9
<212> TYPE: DNA
<213> ORGANISM: Artificial Sequence
<220> FEATURE:
<223> OTHER INFORMATION: made in laboratory

<400> SEQUENCE: 177

gagcgtagc                                                          9


<210> SEQ ID NO 178
<211> LENGTH: 9
<212> TYPE: DNA
<213> ORGANISM: Artificial Sequence
<220> FEATURE:
<223> OTHER INFORMATION: made in laboratory

<400> SEQUENCE: 178

gagcctagc                                                          9


<210> SEQ ID NO 179
<211> LENGTH: 9
<212> TYPE: DNA
<213> ORGANISM: Artificial Sequence
<220> FEATURE:
<223> OTHER INFORMATION: made in laboratory

<400> SEQUENCE: 179

gagcgtagt                                                          9


<210> SEQ ID NO 180
<211> LENGTH: 9
<212> TYPE: DNA
<213> ORGANISM: Artificial Sequence
```

<220> FEATURE:
<223> OTHER INFORMATION: made in laboratory

<400> SEQUENCE: 180 aagcctagc 9

<210> SEQ ID NO 181
<211> LENGTH: 9
<212> TYPE: DNA
<213> ORGANISM: Artificial Sequence
<220> FEATURE:
<223> OTHER INFORMATION: made in laboratory

<400> SEQUENCE: 181 gagcctaga 9

<210> SEQ ID NO 182
<211> LENGTH: 9
<212> TYPE: DNA
<213> ORGANISM: Artificial Sequence
<220> FEATURE:
<223> OTHER INFORMATION: made in laboratory

<400> SEQUENCE: 182 tagcgtagc 9

<210> SEQ ID NO 183
<211> LENGTH: 9
<212> TYPE: DNA
<213> ORGANISM: Artificial Sequence
<220> FEATURE:
<223> OTHER INFORMATION: made in laboratory

<400> SEQUENCE: 183 gagcctagg 9

<210> SEQ ID NO 184
<211> LENGTH: 9
<212> TYPE: DNA
<213> ORGANISM: Artificial Sequence
<220> FEATURE:
<223> OTHER INFORMATION: made in laboratory

<400> SEQUENCE: 184 cagcgtagc 9

<210> SEQ ID NO 185
<211> LENGTH: 9
<212> TYPE: DNA
<213> ORGANISM: Artificial Sequence
<220> FEATURE:
<223> OTHER INFORMATION: made in laboratory

<400> SEQUENCE: 185 gagcctagc 9

<210> SEQ ID NO 186
<211> LENGTH: 9
<212> TYPE: DNA
<213> ORGANISM: Artificial Sequence
<220> FEATURE:
<223> OTHER INFORMATION: made in laboratory

<400> SEQUENCE: 186 gagcgtagc 9

<210> SEQ ID NO 187
<211> LENGTH: 9
<212> TYPE: DNA
<213> ORGANISM: Artificial Sequence
<220> FEATURE:
<223> OTHER INFORMATION: made in laboratory

<400> SEQUENCE: 187 gagcctagt 9

<210> SEQ ID NO 188
<211> LENGTH: 9
<212> TYPE: DNA
<213> ORGANISM: Artificial Sequence
<220> FEATURE:
<223> OTHER INFORMATION: made in laboratory

<400> SEQUENCE: 188 aagcgtagc 9

<210> SEQ ID NO 189
<211> LENGTH: 9
<212> TYPE: DNA
<213> ORGANISM: Artificial Sequence
<220> FEATURE:
<223> OTHER INFORMATION: made in laboratory

<400> SEQUENCE: 189 gagcttaga 9

<210> SEQ ID NO 190
<211> LENGTH: 9
<212> TYPE: DNA
<213> ORGANISM: Artificial Sequence
<220> FEATURE:
<223> OTHER INFORMATION: made in laboratory

<400> SEQUENCE: 190 tagcatagc 9

<210> SEQ ID NO 191
<211> LENGTH: 9
<212> TYPE: DNA
<213> ORGANISM: Artificial Sequence
<220> FEATURE:
<223> OTHER INFORMATION: made in laboratory

<400> SEQUENCE: 191 gagcttagg 9

<210> SEQ ID NO 192
<211> LENGTH: 9
<212> TYPE: DNA
<213> ORGANISM: Artificial Sequence
<220> FEATURE:
<223> OTHER INFORMATION: made in laboratory

<400> SEQUENCE: 192 cagcatagc 9

<210> SEQ ID NO 193
<211> LENGTH: 9
<212> TYPE: DNA
<213> ORGANISM: Artificial Sequence
<220> FEATURE:
<223> OTHER INFORMATION: made in laboratory

<400> SEQUENCE: 193 gagcttagc 9

<210> SEQ ID NO 194
<211> LENGTH: 9
<212> TYPE: DNA
<213> ORGANISM: Artificial Sequence
<220> FEATURE:
<223> OTHER INFORMATION: made in laboratory

<400> SEQUENCE: 194 gagcatagc 9

<210> SEQ ID NO 195
<211> LENGTH: 9
<212> TYPE: DNA
<213> ORGANISM: Artificial Sequence
<220> FEATURE:
<223> OTHER INFORMATION: made in laboratory

<400> SEQUENCE: 195 gagcttagt 9

<210> SEQ ID NO 196
<211> LENGTH: 9
<212> TYPE: DNA
<213> ORGANISM: Artificial Sequence
<220> FEATURE:
<223> OTHER INFORMATION: made in laboratory

<400> SEQUENCE: 196 aagcatagc 9

<210> SEQ ID NO 197
<211> LENGTH: 9
<212> TYPE: DNA
<213> ORGANISM: Artificial Sequence
<220> FEATURE:
<223> OTHER INFORMATION: made in laboratory

<400> SEQUENCE: 197 cagcataga 9

<210> SEQ ID NO 198
<211> LENGTH: 9
<212> TYPE: DNA
<213> ORGANISM: Artificial Sequence
<220> FEATURE:
<223> OTHER INFORMATION: made in laboratory

<400> SEQUENCE: 198 tagcttagg 9

<210> SEQ ID NO 199
<211> LENGTH: 9
<212> TYPE: DNA
<213> ORGANISM: Artificial Sequence
<220> FEATURE:
<223> OTHER INFORMATION: made in laboratory

<400> SEQUENCE: 199 cagcatagg 9

<210> SEQ ID NO 200

<211> LENGTH: 9
<212> TYPE: DNA
<213> ORGANISM: Artificial Sequence
<220> FEATURE:
<223> OTHER INFORMATION: made in laboratory

<400> SEQUENCE: 200 cagcttagg 9

<210> SEQ ID NO 201
<211> LENGTH: 9
<212> TYPE: DNA
<213> ORGANISM: Artificial Sequence
<220> FEATURE:
<223> OTHER INFORMATION: made in laboratory

<400> SEQUENCE: 201 cagcatagc 9

<210> SEQ ID NO 202
<211> LENGTH: 9
<212> TYPE: DNA
<213> ORGANISM: Artificial Sequence
<220> FEATURE:
<223> OTHER INFORMATION: made in laboratory

<400> SEQUENCE: 202 gagcttagg 9

<210> SEQ ID NO 203
<211> LENGTH: 9
<212> TYPE: DNA
<213> ORGANISM: Artificial Sequence
<220> FEATURE:
<223> OTHER INFORMATION: made in laboratory

<400> SEQUENCE: 203 cagcatagt 9

<210> SEQ ID NO 204
<211> LENGTH: 9
<212> TYPE: DNA
<213> ORGANISM: Artificial Sequence
<220> FEATURE:
<223> OTHER INFORMATION: made in laboratory

<400> SEQUENCE: 204 aagcttagg 9

<210> SEQ ID NO 205
<211> LENGTH: 9
<212> TYPE: DNA
<213> ORGANISM: Artificial Sequence
<220> FEATURE:
<223> OTHER INFORMATION: made in laboratory

<400> SEQUENCE: 205 cagcgtaga 9

<210> SEQ ID NO 206
<211> LENGTH: 9
<212> TYPE: DNA
<213> ORGANISM: Artificial Sequence
<220> FEATURE:
<223> OTHER INFORMATION: made in laboratory

<400> SEQUENCE: 206 tagcctagg 9

<210> SEQ ID NO 207
<211> LENGTH: 9
<212> TYPE: DNA
<213> ORGANISM: Artificial Sequence
<220> FEATURE:
<223> OTHER INFORMATION: made in laboratory

<400> SEQUENCE: 207 cagcgtagg 9

<210> SEQ ID NO 208
<211> LENGTH: 9
<212> TYPE: DNA
<213> ORGANISM: Artificial Sequence
<220> FEATURE:
<223> OTHER INFORMATION: made in laboratory

<400> SEQUENCE: 208 cagcctagg 9

<210> SEQ ID NO 209
<211> LENGTH: 9
<212> TYPE: DNA
<213> ORGANISM: Artificial Sequence
<220> FEATURE:
<223> OTHER INFORMATION: made in laboratory

<400> SEQUENCE: 209 cagcgtagc 9

<210> SEQ ID NO 210
<211> LENGTH: 9
<212> TYPE: DNA
<213> ORGANISM: Artificial Sequence
<220> FEATURE:
<223> OTHER INFORMATION: made in laboratory

<400> SEQUENCE: 210 gagcctagg 9

<210> SEQ ID NO 211
<211> LENGTH: 9
<212> TYPE: DNA
<213> ORGANISM: Artificial Sequence
<220> FEATURE:
<223> OTHER INFORMATION: made in laboratory

<400> SEQUENCE: 211 cagcgtagt 9

<210> SEQ ID NO 212
<211> LENGTH: 9
<212> TYPE: DNA
<213> ORGANISM: Artificial Sequence
<220> FEATURE:
<223> OTHER INFORMATION: made in laboratory

<400> SEQUENCE: 212 aagcctagg 9

<210> SEQ ID NO 213
<211> LENGTH: 9
<212> TYPE: DNA

<213> ORGANISM: Artificial Sequence
<220> FEATURE:
<223> OTHER INFORMATION: made in laboratory

<400> SEQUENCE: 213 cagcctaga 9

<210> SEQ ID NO 214
<211> LENGTH: 9
<212> TYPE: DNA
<213> ORGANISM: Artificial Sequence
<220> FEATURE:
<223> OTHER INFORMATION: made in laboratory

<400> SEQUENCE: 214 tagcgtagg 9

<210> SEQ ID NO 215
<211> LENGTH: 9
<212> TYPE: DNA
<213> ORGANISM: Artificial Sequence
<220> FEATURE:
<223> OTHER INFORMATION: made in laboratory

<400> SEQUENCE: 215 cagcctagg 9

<210> SEQ ID NO 216
<211> LENGTH: 9
<212> TYPE: DNA
<213> ORGANISM: Artificial Sequence
<220> FEATURE:
<223> OTHER INFORMATION: made in laboratory

<400> SEQUENCE: 216 cagcgtagg 9

<210> SEQ ID NO 217
<211> LENGTH: 9
<212> TYPE: DNA
<213> ORGANISM: Artificial Sequence
<220> FEATURE:
<223> OTHER INFORMATION: made in laboratory

<400> SEQUENCE: 217 cagcctagc 9

<210> SEQ ID NO 218
<211> LENGTH: 9
<212> TYPE: DNA
<213> ORGANISM: Artificial Sequence
<220> FEATURE:
<223> OTHER INFORMATION: made in laboratory

<400> SEQUENCE: 218 gagcgtagg 9

<210> SEQ ID NO 219
<211> LENGTH: 9
<212> TYPE: DNA
<213> ORGANISM: Artificial Sequence
<220> FEATURE:
<223> OTHER INFORMATION: made in laboratory

<400> SEQUENCE: 219 cagcctagt 9

<210> SEQ ID NO 220
<211> LENGTH: 9
<212> TYPE: DNA
<213> ORGANISM: Artificial Sequence
<220> FEATURE:
<223> OTHER INFORMATION: made in laboratory

<400> SEQUENCE: 220 aagcgtagg 9

<210> SEQ ID NO 221
<211> LENGTH: 9
<212> TYPE: DNA
<213> ORGANISM: Artificial Sequence
<220> FEATURE:
<223> OTHER INFORMATION: made in laboratory

<400> SEQUENCE: 221 cagcttaga 9

<210> SEQ ID NO 222
<211> LENGTH: 9
<212> TYPE: DNA
<213> ORGANISM: Artificial Sequence
<220> FEATURE:
<223> OTHER INFORMATION: made in laboratory

<400> SEQUENCE: 222 tagcatagg 9

<210> SEQ ID NO 223
<211> LENGTH: 9
<212> TYPE: DNA
<213> ORGANISM: Artificial Sequence
<220> FEATURE:
<223> OTHER INFORMATION: made in laboratory

<400> SEQUENCE: 223 cagcttagg 9

<210> SEQ ID NO 224
<211> LENGTH: 9
<212> TYPE: DNA
<213> ORGANISM: Artificial Sequence
<220> FEATURE:
<223> OTHER INFORMATION: made in laboratory

<400> SEQUENCE: 224 cagcatagg 9

<210> SEQ ID NO 225
<211> LENGTH: 9
<212> TYPE: DNA
<213> ORGANISM: Artificial Sequence
<220> FEATURE:
<223> OTHER INFORMATION: made in laboratory

<400> SEQUENCE: 225 cagcttagc 9

<210> SEQ ID NO 226
<211> LENGTH: 9
<212> TYPE: DNA
<213> ORGANISM: Artificial Sequence
<220> FEATURE:

<223> OTHER INFORMATION: made in laboratory

<400> SEQUENCE: 226 gagcatagg 9

<210> SEQ ID NO 227
<211> LENGTH: 9
<212> TYPE: DNA
<213> ORGANISM: Artificial Sequence
<220> FEATURE:
<223> OTHER INFORMATION: made in laboratory

<400> SEQUENCE: 227 cagcttagt 9

<210> SEQ ID NO 228
<211> LENGTH: 9
<212> TYPE: DNA
<213> ORGANISM: Artificial Sequence
<220> FEATURE:
<223> OTHER INFORMATION: made in laboratory

<400> SEQUENCE: 228 aagcatagg 9

<210> SEQ ID NO 229
<211> LENGTH: 9
<212> TYPE: DNA
<213> ORGANISM: Artificial Sequence
<220> FEATURE:
<223> OTHER INFORMATION: made in laboratory

<400> SEQUENCE: 229 tagcataga 9

<210> SEQ ID NO 230
<211> LENGTH: 9
<212> TYPE: DNA
<213> ORGANISM: Artificial Sequence
<220> FEATURE:
<223> OTHER INFORMATION: made in laboratory

<400> SEQUENCE: 230 tagcttaga 9

<210> SEQ ID NO 231
<211> LENGTH: 9
<212> TYPE: DNA
<213> ORGANISM: Artificial Sequence
<220> FEATURE:
<223> OTHER INFORMATION: made in laboratory

<400> SEQUENCE: 231 tagcatagg 9

<210> SEQ ID NO 232
<211> LENGTH: 9
<212> TYPE: DNA
<213> ORGANISM: Artificial Sequence
<220> FEATURE:
<223> OTHER INFORMATION: made in laboratory

<400> SEQUENCE: 232 cagcttaga 9

<210> SEQ ID NO 233
<211> LENGTH: 9
<212> TYPE: DNA
<213> ORGANISM: Artificial Sequence
<220> FEATURE:
<223> OTHER INFORMATION: made in laboratory

<400> SEQUENCE: 233 tagcatagc 9

<210> SEQ ID NO 234
<211> LENGTH: 9
<212> TYPE: DNA
<213> ORGANISM: Artificial Sequence
<220> FEATURE:
<223> OTHER INFORMATION: made in laboratory

<400> SEQUENCE: 234 gagcttaga 9

<210> SEQ ID NO 235
<211> LENGTH: 9
<212> TYPE: DNA
<213> ORGANISM: Artificial Sequence
<220> FEATURE:
<223> OTHER INFORMATION: made in laboratory

<400> SEQUENCE: 235 tagcatagt 9

<210> SEQ ID NO 236
<211> LENGTH: 9
<212> TYPE: DNA
<213> ORGANISM: Artificial Sequence
<220> FEATURE:
<223> OTHER INFORMATION: made in laboratory

<400> SEQUENCE: 236 aagcttaga 9

<210> SEQ ID NO 237
<211> LENGTH: 9
<212> TYPE: DNA
<213> ORGANISM: Artificial Sequence
<220> FEATURE:
<223> OTHER INFORMATION: made in laboratory

<400> SEQUENCE: 237 tagcgtaga 9

<210> SEQ ID NO 238
<211> LENGTH: 9
<212> TYPE: DNA
<213> ORGANISM: Artificial Sequence
<220> FEATURE:
<223> OTHER INFORMATION: made in laboratory

<400> SEQUENCE: 238 tagcctaga 9

<210> SEQ ID NO 239
<211> LENGTH: 9
<212> TYPE: DNA
<213> ORGANISM: Artificial Sequence
<220> FEATURE:
<223> OTHER INFORMATION: made in laboratory

<400> SEQUENCE: 239 tagcgtagg 9

<210> SEQ ID NO 240
<211> LENGTH: 9
<212> TYPE: DNA
<213> ORGANISM: Artificial Sequence
<220> FEATURE:
<223> OTHER INFORMATION: made in laboratory

<400> SEQUENCE: 240 cagcctaga 9

<210> SEQ ID NO 241
<211> LENGTH: 9
<212> TYPE: DNA
<213> ORGANISM: Artificial Sequence
<220> FEATURE:
<223> OTHER INFORMATION: made in laboratory

<400> SEQUENCE: 241 tagcgtagc 9

<210> SEQ ID NO 242
<211> LENGTH: 9
<212> TYPE: DNA
<213> ORGANISM: Artificial Sequence
<220> FEATURE:
<223> OTHER INFORMATION: made in laboratory

<400> SEQUENCE: 242 gagcctaga 9

<210> SEQ ID NO 243
<211> LENGTH: 9
<212> TYPE: DNA
<213> ORGANISM: Artificial Sequence
<220> FEATURE:
<223> OTHER INFORMATION: made in laboratory

<400> SEQUENCE: 243 tagcgtagt 9

<210> SEQ ID NO 244
<211> LENGTH: 9
<212> TYPE: DNA
<213> ORGANISM: Artificial Sequence
<220> FEATURE:
<223> OTHER INFORMATION: made in laboratory

<400> SEQUENCE: 244 aagcctaga 9

<210> SEQ ID NO 245
<211> LENGTH: 9
<212> TYPE: DNA
<213> ORGANISM: Artificial Sequence
<220> FEATURE:
<223> OTHER INFORMATION: made in laboratory

<400> SEQUENCE: 245 tagcctaga 9

<210> SEQ ID NO 246
<211> LENGTH: 9

<212> TYPE: DNA
<213> ORGANISM: Artificial Sequence
<220> FEATURE:
<223> OTHER INFORMATION: made in laboratory

<400> SEQUENCE: 246 tagcgtaga 9

<210> SEQ ID NO 247
<211> LENGTH: 9
<212> TYPE: DNA
<213> ORGANISM: Artificial Sequence
<220> FEATURE:
<223> OTHER INFORMATION: made in laboratory

<400> SEQUENCE: 247 tagcctagg 9

<210> SEQ ID NO 248
<211> LENGTH: 9
<212> TYPE: DNA
<213> ORGANISM: Artificial Sequence
<220> FEATURE:
<223> OTHER INFORMATION: made in laboratory

<400> SEQUENCE: 248 cagcgtaga 9

<210> SEQ ID NO 249
<211> LENGTH: 9
<212> TYPE: DNA
<213> ORGANISM: Artificial Sequence
<220> FEATURE:
<223> OTHER INFORMATION: made in laboratory

<400> SEQUENCE: 249 tagcctagc 9

<210> SEQ ID NO 250
<211> LENGTH: 9
<212> TYPE: DNA
<213> ORGANISM: Artificial Sequence
<220> FEATURE:
<223> OTHER INFORMATION: made in laboratory

<400> SEQUENCE: 250 gagcgtaga 9

<210> SEQ ID NO 251
<211> LENGTH: 9
<212> TYPE: DNA
<213> ORGANISM: Artificial Sequence
<220> FEATURE:
<223> OTHER INFORMATION: made in laboratory

<400> SEQUENCE: 251 tagcctagt 9

<210> SEQ ID NO 252
<211> LENGTH: 9
<212> TYPE: DNA
<213> ORGANISM: Artificial Sequence
<220> FEATURE:
<223> OTHER INFORMATION: made in laboratory

<400> SEQUENCE: 252 aagcgtaga 9

<210> SEQ ID NO 253
<211> LENGTH: 9
<212> TYPE: DNA
<213> ORGANISM: Artificial Sequence
<220> FEATURE:
<223> OTHER INFORMATION: made in laboratory

<400> SEQUENCE: 253 tagcttaga 9

<210> SEQ ID NO 254
<211> LENGTH: 9
<212> TYPE: DNA
<213> ORGANISM: Artificial Sequence
<220> FEATURE:
<223> OTHER INFORMATION: made in laboratory

<400> SEQUENCE: 254 tagcataga 9

<210> SEQ ID NO 255
<211> LENGTH: 9
<212> TYPE: DNA
<213> ORGANISM: Artificial Sequence
<220> FEATURE:
<223> OTHER INFORMATION: made in laboratory

<400> SEQUENCE: 255 tagcttagg 9

<210> SEQ ID NO 256
<211> LENGTH: 9
<212> TYPE: DNA
<213> ORGANISM: Artificial Sequence
<220> FEATURE:
<223> OTHER INFORMATION: made in laboratory

<400> SEQUENCE: 256 cagcataga 9

<210> SEQ ID NO 257
<211> LENGTH: 9
<212> TYPE: DNA
<213> ORGANISM: Artificial Sequence
<220> FEATURE:
<223> OTHER INFORMATION: made in laboratory

<400> SEQUENCE: 257 tagcttagc 9

<210> SEQ ID NO 258
<211> LENGTH: 9
<212> TYPE: DNA
<213> ORGANISM: Artificial Sequence
<220> FEATURE:
<223> OTHER INFORMATION: made in laboratory

<400> SEQUENCE: 258 gagcataga 9

<210> SEQ ID NO 259
<211> LENGTH: 9
<212> TYPE: DNA
<213> ORGANISM: Artificial Sequence
<220> FEATURE:
<223> OTHER INFORMATION: made in laboratory

<400> SEQUENCE: 259 tagcttagt 9

<210> SEQ ID NO 260
<211> LENGTH: 9
<212> TYPE: DNA
<213> ORGANISM: Artificial Sequence
<220> FEATURE:
<223> OTHER INFORMATION: made in laboratory

<400> SEQUENCE: 260 aagcataga 9

<210> SEQ ID NO 261
<211> LENGTH: 76
<212> TYPE: DNA
<213> ORGANISM: Artificial Sequence
<220> FEATURE:
<223> OTHER INFORMATION: made in laboratory
<220> FEATURE:
<221> NAME/KEY: misc_feature
<222> LOCATION: (26)..(33)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t

<400> SEQUENCE: 261
aatgatacgg cgaccaccga gatctnnnnn nnnacactct ttccctacac gacgctcttc 60
cgatcnagct nagctn 76

<210> SEQ ID NO 262
<211> LENGTH: 75
<212> TYPE: DNA
<213> ORGANISM: Artificial Sequence
<220> FEATURE:
<223> OTHER INFORMATION: made in laboratory
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (45)..(52)
<223> OTHER INFORMATION: n is a, c, g, or t

<400> SEQUENCE: 262
nagctnagct ngatcggaag agcacacgtc tgaactccag tcacnnnnnn nnatctcgta 60
tgccgtcttc tgctt 75

<210> SEQ ID NO 263
<211> LENGTH: 11
<212> TYPE: DNA
<213> ORGANISM: Artificial Sequence
<220> FEATURE:
<223> OTHER INFORMATION: made in laboratory

<400> SEQUENCE: 263
aagctaagct a 11

<210> SEQ ID NO 264
<211> LENGTH: 11
<212> TYPE: DNA
<213> ORGANISM: Artificial Sequence
<220> FEATURE:
<223> OTHER INFORMATION: made in laboratory

<400> SEQUENCE: 264
tagcttagct t 11

<210> SEQ ID NO 265
<211> LENGTH: 11
<212> TYPE: DNA
<213> ORGANISM: Artificial Sequence
<220> FEATURE:
<223> OTHER INFORMATION: made in laboratory

<400> SEQUENCE: 265
aagctaagct g 11

<210> SEQ ID NO 266
<211> LENGTH: 11
<212> TYPE: DNA
<213> ORGANISM: Artificial Sequence
<220> FEATURE:
<223> OTHER INFORMATION: made in laboratory

<400> SEQUENCE: 266
cagcttagct t 11

<210> SEQ ID NO 267
<211> LENGTH: 11
<212> TYPE: DNA
<213> ORGANISM: Artificial Sequence
<220> FEATURE:
<223> OTHER INFORMATION: made in laboratory

<400> SEQUENCE: 267
aagctaagct c 11

<210> SEQ ID NO 268
<211> LENGTH: 11
<212> TYPE: DNA
<213> ORGANISM: Artificial Sequence
<220> FEATURE:
<223> OTHER INFORMATION: made in laboratory

<400> SEQUENCE: 268
gagcttagct t 11

<210> SEQ ID NO 269
<211> LENGTH: 11
<212> TYPE: DNA
<213> ORGANISM: Artificial Sequence
<220> FEATURE:
<223> OTHER INFORMATION: made in laboratory

<400> SEQUENCE: 269
aagctaagct t 11

<210> SEQ ID NO 270
<211> LENGTH: 11
<212> TYPE: DNA
<213> ORGANISM: Artificial Sequence
<220> FEATURE:
<223> OTHER INFORMATION: made in laboratory

<400> SEQUENCE: 270
aagcttagct t 11

<210> SEQ ID NO 271
<211> LENGTH: 11
<212> TYPE: DNA
<213> ORGANISM: Artificial Sequence
<220> FEATURE:
<223> OTHER INFORMATION: made in laboratory

<400> SEQUENCE: 271
aagctgagct a 11

<210> SEQ ID NO 272
<211> LENGTH: 11
<212> TYPE: DNA
<213> ORGANISM: Artificial Sequence
<220> FEATURE:
<223> OTHER INFORMATION: made in laboratory

<400> SEQUENCE: 272
tagctcagct t 11

<210> SEQ ID NO 273
<211> LENGTH: 11
<212> TYPE: DNA
<213> ORGANISM: Artificial Sequence
<220> FEATURE:
<223> OTHER INFORMATION: made in laboratory

<400> SEQUENCE: 273
aagctgagct g 11

<210> SEQ ID NO 274
<211> LENGTH: 11
<212> TYPE: DNA
<213> ORGANISM: Artificial Sequence
<220> FEATURE:
<223> OTHER INFORMATION: made in laboratory

<400> SEQUENCE: 274
cagctcagct t 11

<210> SEQ ID NO 275
<211> LENGTH: 11
<212> TYPE: DNA
<213> ORGANISM: Artificial Sequence
<220> FEATURE:
<223> OTHER INFORMATION: made in laboratory

<400> SEQUENCE: 275
aagctgagct c 11

<210> SEQ ID NO 276

<211> LENGTH: 11
<212> TYPE: DNA
<213> ORGANISM: Artificial Sequence
<220> FEATURE:
<223> OTHER INFORMATION: made in laboratory

<400> SEQUENCE: 276
gagctcagct t 11

<210> SEQ ID NO 277
<211> LENGTH: 11
<212> TYPE: DNA
<213> ORGANISM: Artificial Sequence
<220> FEATURE:
<223> OTHER INFORMATION: made in laboratory

<400> SEQUENCE: 277
aagctgagct t 11

<210> SEQ ID NO 278
<211> LENGTH: 11
<212> TYPE: DNA
<213> ORGANISM: Artificial Sequence
<220> FEATURE:
<223> OTHER INFORMATION: made in laboratory

<400> SEQUENCE: 278
aagctcagct t 11

<210> SEQ ID NO 279
<211> LENGTH: 11
<212> TYPE: DNA
<213> ORGANISM: Artificial Sequence
<220> FEATURE:
<223> OTHER INFORMATION: made in laboratory

<400> SEQUENCE: 279
aagctcagct a 11

<210> SEQ ID NO 280
<211> LENGTH: 11
<212> TYPE: DNA
<213> ORGANISM: Artificial Sequence
<220> FEATURE:
<223> OTHER INFORMATION: made in laboratory

<400> SEQUENCE: 280
tagctgagct t 11

<210> SEQ ID NO 281
<211> LENGTH: 11
<212> TYPE: DNA
<213> ORGANISM: Artificial Sequence
<220> FEATURE:
<223> OTHER INFORMATION: made in laboratory

<400> SEQUENCE: 281
aagctcagct g 11

<210> SEQ ID NO 282
<211> LENGTH: 11
<212> TYPE: DNA
<213> ORGANISM: Artificial Sequence
<220> FEATURE:
<223> OTHER INFORMATION: made in laboratory

<400> SEQUENCE: 282
cagctgagct t 11

<210> SEQ ID NO 283
<211> LENGTH: 11
<212> TYPE: DNA
<213> ORGANISM: Artificial Sequence
<220> FEATURE:
<223> OTHER INFORMATION: made in laboratory

<400> SEQUENCE: 283
aagctcagct c 11

<210> SEQ ID NO 284
<211> LENGTH: 11
<212> TYPE: DNA
<213> ORGANISM: Artificial Sequence
<220> FEATURE:
<223> OTHER INFORMATION: made in laboratory

<400> SEQUENCE: 284
gagctgagct t 11

<210> SEQ ID NO 285
<211> LENGTH: 11
<212> TYPE: DNA
<213> ORGANISM: Artificial Sequence
<220> FEATURE:
<223> OTHER INFORMATION: made in laboratory

<400> SEQUENCE: 285
aagctcagct t 11

<210> SEQ ID NO 286
<211> LENGTH: 11
<212> TYPE: DNA
<213> ORGANISM: Artificial Sequence
<220> FEATURE:
<223> OTHER INFORMATION: made in laboratory

<400> SEQUENCE: 286
aagctgagct t 11

<210> SEQ ID NO 287
<211> LENGTH: 11
<212> TYPE: DNA
<213> ORGANISM: Artificial Sequence
<220> FEATURE:
<223> OTHER INFORMATION: made in laboratory

<400> SEQUENCE: 287
aagcttagct a 11

<210> SEQ ID NO 288
<211> LENGTH: 11
<212> TYPE: DNA
<213> ORGANISM: Artificial Sequence
<220> FEATURE:
<223> OTHER INFORMATION: made in laboratory

<400> SEQUENCE: 288
tagctaagct t 11

<210> SEQ ID NO 289
<211> LENGTH: 11
<212> TYPE: DNA

<213> ORGANISM: Artificial Sequence
<220> FEATURE:
<223> OTHER INFORMATION: made in laboratory

<400> SEQUENCE: 289
aagcttagct g 11

<210> SEQ ID NO 290
<211> LENGTH: 11
<212> TYPE: DNA
<213> ORGANISM: Artificial Sequence
<220> FEATURE:
<223> OTHER INFORMATION: made in laboratory

<400> SEQUENCE: 290
cagctaagct t 11

<210> SEQ ID NO 291
<211> LENGTH: 11
<212> TYPE: DNA
<213> ORGANISM: Artificial Sequence
<220> FEATURE:
<223> OTHER INFORMATION: made in laboratory

<400> SEQUENCE: 291
aagcttagct c 11

<210> SEQ ID NO 292
<211> LENGTH: 11
<212> TYPE: DNA
<213> ORGANISM: Artificial Sequence
<220> FEATURE:
<223> OTHER INFORMATION: made in laboratory

<400> SEQUENCE: 292
gagctaagct t 11

<210> SEQ ID NO 293
<211> LENGTH: 11
<212> TYPE: DNA
<213> ORGANISM: Artificial Sequence
<220> FEATURE:
<223> OTHER INFORMATION: made in laboratory

<400> SEQUENCE: 293
aagcttagct t 11

<210> SEQ ID NO 294
<211> LENGTH: 11
<212> TYPE: DNA
<213> ORGANISM: Artificial Sequence
<220> FEATURE:
<223> OTHER INFORMATION: made in laboratory

<400> SEQUENCE: 294
aagctaagct t 11

<210> SEQ ID NO 295
<211> LENGTH: 11
<212> TYPE: DNA
<213> ORGANISM: Artificial Sequence
<220> FEATURE:
<223> OTHER INFORMATION: made in laboratory

<400> SEQUENCE: 295
gagctaagct a 11

<210> SEQ ID NO 296
<211> LENGTH: 11
<212> TYPE: DNA
<213> ORGANISM: Artificial Sequence
<220> FEATURE:
<223> OTHER INFORMATION: made in laboratory

<400> SEQUENCE: 296
tagcttagct c 11

<210> SEQ ID NO 297
<211> LENGTH: 11
<212> TYPE: DNA
<213> ORGANISM: Artificial Sequence
<220> FEATURE:
<223> OTHER INFORMATION: made in laboratory

<400> SEQUENCE: 297
gagctaagct g 11

<210> SEQ ID NO 298
<211> LENGTH: 11
<212> TYPE: DNA
<213> ORGANISM: Artificial Sequence
<220> FEATURE:
<223> OTHER INFORMATION: made in laboratory

<400> SEQUENCE: 298
cagcttagct c 11

<210> SEQ ID NO 299
<211> LENGTH: 11
<212> TYPE: DNA
<213> ORGANISM: Artificial Sequence
<220> FEATURE:
<223> OTHER INFORMATION: made in laboratory

<400> SEQUENCE: 299
gagctaagct c 11

<210> SEQ ID NO 300
<211> LENGTH: 11
<212> TYPE: DNA
<213> ORGANISM: Artificial Sequence
<220> FEATURE:
<223> OTHER INFORMATION: made in laboratory

<400> SEQUENCE: 300
gagcttagct c 11

<210> SEQ ID NO 301
<211> LENGTH: 11
<212> TYPE: DNA
<213> ORGANISM: Artificial Sequence
<220> FEATURE:
<223> OTHER INFORMATION: made in laboratory

<400> SEQUENCE: 301
gagctaagct t 11

<210> SEQ ID NO 302
<211> LENGTH: 11
<212> TYPE: DNA
<213> ORGANISM: Artificial Sequence
<220> FEATURE:

<223> OTHER INFORMATION: made in laboratory

<400> SEQUENCE: 302
aagcttagct c 11

<210> SEQ ID NO 303
<211> LENGTH: 11
<212> TYPE: DNA
<213> ORGANISM: Artificial Sequence
<220> FEATURE:
<223> OTHER INFORMATION: made in laboratory

<400> SEQUENCE: 303
gagctgagct a 11

<210> SEQ ID NO 304
<211> LENGTH: 11
<212> TYPE: DNA
<213> ORGANISM: Artificial Sequence
<220> FEATURE:
<223> OTHER INFORMATION: made in laboratory

<400> SEQUENCE: 304
tagctcagct c 11

<210> SEQ ID NO 305
<211> LENGTH: 11
<212> TYPE: DNA
<213> ORGANISM: Artificial Sequence
<220> FEATURE:
<223> OTHER INFORMATION: made in laboratory

<400> SEQUENCE: 305
gagctgagct g 11

<210> SEQ ID NO 306
<211> LENGTH: 11
<212> TYPE: DNA
<213> ORGANISM: Artificial Sequence
<220> FEATURE:
<223> OTHER INFORMATION: made in laboratory

<400> SEQUENCE: 306
cagctcagct c 11

<210> SEQ ID NO 307
<211> LENGTH: 11
<212> TYPE: DNA
<213> ORGANISM: Artificial Sequence
<220> FEATURE:
<223> OTHER INFORMATION: made in laboratory

<400> SEQUENCE: 307
gagctgagct c 11

<210> SEQ ID NO 308
<211> LENGTH: 11
<212> TYPE: DNA
<213> ORGANISM: Artificial Sequence
<220> FEATURE:
<223> OTHER INFORMATION: made in laboratory

<400> SEQUENCE: 308
gagctcagct c 11

<210> SEQ ID NO 309
<211> LENGTH: 11
<212> TYPE: DNA
<213> ORGANISM: Artificial Sequence
<220> FEATURE:
<223> OTHER INFORMATION: made in laboratory

<400> SEQUENCE: 309
gagctgagct t 11

<210> SEQ ID NO 310
<211> LENGTH: 11
<212> TYPE: DNA
<213> ORGANISM: Artificial Sequence
<220> FEATURE:
<223> OTHER INFORMATION: made in laboratory

<400> SEQUENCE: 310
aagctcagct c 11

<210> SEQ ID NO 311
<211> LENGTH: 11
<212> TYPE: DNA
<213> ORGANISM: Artificial Sequence
<220> FEATURE:
<223> OTHER INFORMATION: made in laboratory

<400> SEQUENCE: 311
gagctcagct a 11

<210> SEQ ID NO 312
<211> LENGTH: 11
<212> TYPE: DNA
<213> ORGANISM: Artificial Sequence
<220> FEATURE:
<223> OTHER INFORMATION: made in laboratory

<400> SEQUENCE: 312
tagctgagct c 11

<210> SEQ ID NO 313
<211> LENGTH: 11
<212> TYPE: DNA
<213> ORGANISM: Artificial Sequence
<220> FEATURE:
<223> OTHER INFORMATION: made in laboratory

<400> SEQUENCE: 313
gagctcagct g 11

<210> SEQ ID NO 314
<211> LENGTH: 11
<212> TYPE: DNA
<213> ORGANISM: Artificial Sequence
<220> FEATURE:
<223> OTHER INFORMATION: made in laboratory

<400> SEQUENCE: 314
cagctgagct c 11

<210> SEQ ID NO 315
<211> LENGTH: 11
<212> TYPE: DNA
<213> ORGANISM: Artificial Sequence
<220> FEATURE:
<223> OTHER INFORMATION: made in laboratory

<400> SEQUENCE: 315
gagctcagct c 11

<210> SEQ ID NO 316
<211> LENGTH: 11
<212> TYPE: DNA
<213> ORGANISM: Artificial Sequence
<220> FEATURE:
<223> OTHER INFORMATION: made in laboratory

<400> SEQUENCE: 316
gagctgagct c 11

<210> SEQ ID NO 317
<211> LENGTH: 11
<212> TYPE: DNA
<213> ORGANISM: Artificial Sequence
<220> FEATURE:
<223> OTHER INFORMATION: made in laboratory

<400> SEQUENCE: 317
gagctcagct t 11

<210> SEQ ID NO 318
<211> LENGTH: 11
<212> TYPE: DNA
<213> ORGANISM: Artificial Sequence
<220> FEATURE:
<223> OTHER INFORMATION: made in laboratory

<400> SEQUENCE: 318
aagctgagct c 11

<210> SEQ ID NO 319
<211> LENGTH: 11
<212> TYPE: DNA
<213> ORGANISM: Artificial Sequence
<220> FEATURE:
<223> OTHER INFORMATION: made in laboratory

<400> SEQUENCE: 319
gagcttagct a 11

<210> SEQ ID NO 320
<211> LENGTH: 11
<212> TYPE: DNA
<213> ORGANISM: Artificial Sequence
<220> FEATURE:
<223> OTHER INFORMATION: made in laboratory

<400> SEQUENCE: 320
tagctaagct c 11

<210> SEQ ID NO 321
<211> LENGTH: 11
<212> TYPE: DNA
<213> ORGANISM: Artificial Sequence
<220> FEATURE:
<223> OTHER INFORMATION: made in laboratory

<400> SEQUENCE: 321
gagcttagct g 11

<210> SEQ ID NO 322
<211> LENGTH: 11

<212> TYPE: DNA
<213> ORGANISM: Artificial Sequence
<220> FEATURE:
<223> OTHER INFORMATION: made in laboratory

<400> SEQUENCE: 322
cagctaagct c 11

<210> SEQ ID NO 323
<211> LENGTH: 11
<212> TYPE: DNA
<213> ORGANISM: Artificial Sequence
<220> FEATURE:
<223> OTHER INFORMATION: made in laboratory

<400> SEQUENCE: 323
gagcttagct c 11

<210> SEQ ID NO 324
<211> LENGTH: 11
<212> TYPE: DNA
<213> ORGANISM: Artificial Sequence
<220> FEATURE:
<223> OTHER INFORMATION: made in laboratory

<400> SEQUENCE: 324
gagctaagct c 11

<210> SEQ ID NO 325
<211> LENGTH: 11
<212> TYPE: DNA
<213> ORGANISM: Artificial Sequence
<220> FEATURE:
<223> OTHER INFORMATION: made in laboratory

<400> SEQUENCE: 325
gagcttagct t 11

<210> SEQ ID NO 326
<211> LENGTH: 11
<212> TYPE: DNA
<213> ORGANISM: Artificial Sequence
<220> FEATURE:
<223> OTHER INFORMATION: made in laboratory

<400> SEQUENCE: 326
aagctaagct c 11

<210> SEQ ID NO 327
<211> LENGTH: 11
<212> TYPE: DNA
<213> ORGANISM: Artificial Sequence
<220> FEATURE:
<223> OTHER INFORMATION: made in laboratory

<400> SEQUENCE: 327
cagctaagct a 11

<210> SEQ ID NO 328
<211> LENGTH: 11
<212> TYPE: DNA
<213> ORGANISM: Artificial Sequence
<220> FEATURE:
<223> OTHER INFORMATION: made in laboratory

<400> SEQUENCE: 328

```
tagcttagct g                                                            11


<210> SEQ ID NO 329
<211> LENGTH: 11
<212> TYPE: DNA
<213> ORGANISM: Artificial Sequence
<220> FEATURE:
<223> OTHER INFORMATION: made in laboratory

<400> SEQUENCE: 329

cagctaagct g                                                            11


<210> SEQ ID NO 330
<211> LENGTH: 11
<212> TYPE: DNA
<213> ORGANISM: Artificial Sequence
<220> FEATURE:
<223> OTHER INFORMATION: made in laboratory

<400> SEQUENCE: 330

cagcttagct g                                                            11


<210> SEQ ID NO 331
<211> LENGTH: 11
<212> TYPE: DNA
<213> ORGANISM: Artificial Sequence
<220> FEATURE:
<223> OTHER INFORMATION: made in laboratory

<400> SEQUENCE: 331

cagctaagct c                                                            11


<210> SEQ ID NO 332
<211> LENGTH: 11
<212> TYPE: DNA
<213> ORGANISM: Artificial Sequence
<220> FEATURE:
<223> OTHER INFORMATION: made in laboratory

<400> SEQUENCE: 332

gagcttagct g                                                            11


<210> SEQ ID NO 333
<211> LENGTH: 11
<212> TYPE: DNA
<213> ORGANISM: Artificial Sequence
<220> FEATURE:
<223> OTHER INFORMATION: made in laboratory

<400> SEQUENCE: 333

cagctaagct t                                                            11


<210> SEQ ID NO 334
<211> LENGTH: 11
<212> TYPE: DNA
<213> ORGANISM: Artificial Sequence
<220> FEATURE:
<223> OTHER INFORMATION: made in laboratory

<400> SEQUENCE: 334

aagcttagct g                                                            11


<210> SEQ ID NO 335
<211> LENGTH: 11
<212> TYPE: DNA
<213> ORGANISM: Artificial Sequence
```

<220> FEATURE:
<223> OTHER INFORMATION: made in laboratory

<400> SEQUENCE: 335
cagctgagct a 11

<210> SEQ ID NO 336
<211> LENGTH: 11
<212> TYPE: DNA
<213> ORGANISM: Artificial Sequence
<220> FEATURE:
<223> OTHER INFORMATION: made in laboratory

<400> SEQUENCE: 336
tagctcagct g 11

<210> SEQ ID NO 337
<211> LENGTH: 11
<212> TYPE: DNA
<213> ORGANISM: Artificial Sequence
<220> FEATURE:
<223> OTHER INFORMATION: made in laboratory

<400> SEQUENCE: 337
cagctgagct g 11

<210> SEQ ID NO 338
<211> LENGTH: 11
<212> TYPE: DNA
<213> ORGANISM: Artificial Sequence
<220> FEATURE:
<223> OTHER INFORMATION: made in laboratory

<400> SEQUENCE: 338
cagctcagct g 11

<210> SEQ ID NO 339
<211> LENGTH: 11
<212> TYPE: DNA
<213> ORGANISM: Artificial Sequence
<220> FEATURE:
<223> OTHER INFORMATION: made in laboratory

<400> SEQUENCE: 339
cagctgagct c 11

<210> SEQ ID NO 340
<211> LENGTH: 11
<212> TYPE: DNA
<213> ORGANISM: Artificial Sequence
<220> FEATURE:
<223> OTHER INFORMATION: made in laboratory

<400> SEQUENCE: 340
gagctcagct g 11

<210> SEQ ID NO 341
<211> LENGTH: 11
<212> TYPE: DNA
<213> ORGANISM: Artificial Sequence
<220> FEATURE:
<223> OTHER INFORMATION: made in laboratory

<400> SEQUENCE: 341
cagctgagct t 11

<210> SEQ ID NO 342
<211> LENGTH: 11
<212> TYPE: DNA
<213> ORGANISM: Artificial Sequence
<220> FEATURE:
<223> OTHER INFORMATION: made in laboratory

<400> SEQUENCE: 342
aagctcagct g 11

<210> SEQ ID NO 343
<211> LENGTH: 11
<212> TYPE: DNA
<213> ORGANISM: Artificial Sequence
<220> FEATURE:
<223> OTHER INFORMATION: made in laboratory

<400> SEQUENCE: 343
cagctcagct a 11

<210> SEQ ID NO 344
<211> LENGTH: 11
<212> TYPE: DNA
<213> ORGANISM: Artificial Sequence
<220> FEATURE:
<223> OTHER INFORMATION: made in laboratory

<400> SEQUENCE: 344
tagctgagct g 11

<210> SEQ ID NO 345
<211> LENGTH: 11
<212> TYPE: DNA
<213> ORGANISM: Artificial Sequence
<220> FEATURE:
<223> OTHER INFORMATION: made in laboratory

<400> SEQUENCE: 345
cagctcagct g 11

<210> SEQ ID NO 346
<211> LENGTH: 11
<212> TYPE: DNA
<213> ORGANISM: Artificial Sequence
<220> FEATURE:
<223> OTHER INFORMATION: made in laboratory

<400> SEQUENCE: 346
cagctgagct g 11

<210> SEQ ID NO 347
<211> LENGTH: 11
<212> TYPE: DNA
<213> ORGANISM: Artificial Sequence
<220> FEATURE:
<223> OTHER INFORMATION: made in laboratory

<400> SEQUENCE: 347
cagctcagct c 11

<210> SEQ ID NO 348
<211> LENGTH: 11
<212> TYPE: DNA
<213> ORGANISM: Artificial Sequence
<220> FEATURE:
<223> OTHER INFORMATION: made in laboratory

<400> SEQUENCE: 348
gagctgagct g 11

<210> SEQ ID NO 349
<211> LENGTH: 11
<212> TYPE: DNA
<213> ORGANISM: Artificial Sequence
<220> FEATURE:
<223> OTHER INFORMATION: made in laboratory

<400> SEQUENCE: 349
cagctcagct t 11

<210> SEQ ID NO 350
<211> LENGTH: 11
<212> TYPE: DNA
<213> ORGANISM: Artificial Sequence
<220> FEATURE:
<223> OTHER INFORMATION: made in laboratory

<400> SEQUENCE: 350
aagctgagct g 11

<210> SEQ ID NO 351
<211> LENGTH: 11
<212> TYPE: DNA
<213> ORGANISM: Artificial Sequence
<220> FEATURE:
<223> OTHER INFORMATION: made in laboratory

<400> SEQUENCE: 351
cagcttagct a 11

<210> SEQ ID NO 352
<211> LENGTH: 11
<212> TYPE: DNA
<213> ORGANISM: Artificial Sequence
<220> FEATURE:
<223> OTHER INFORMATION: made in laboratory

<400> SEQUENCE: 352
tagctaagct g 11

<210> SEQ ID NO 353
<211> LENGTH: 11
<212> TYPE: DNA
<213> ORGANISM: Artificial Sequence
<220> FEATURE:
<223> OTHER INFORMATION: made in laboratory

<400> SEQUENCE: 353
cagcttagct g 11

<210> SEQ ID NO 354
<211> LENGTH: 11
<212> TYPE: DNA
<213> ORGANISM: Artificial Sequence
<220> FEATURE:
<223> OTHER INFORMATION: made in laboratory

<400> SEQUENCE: 354
cagctaagct g 11

<210> SEQ ID NO 355

<211> LENGTH: 11
<212> TYPE: DNA
<213> ORGANISM: Artificial Sequence
<220> FEATURE:
<223> OTHER INFORMATION: made in laboratory

<400> SEQUENCE: 355
cagcttagct c 11

<210> SEQ ID NO 356
<211> LENGTH: 11
<212> TYPE: DNA
<213> ORGANISM: Artificial Sequence
<220> FEATURE:
<223> OTHER INFORMATION: made in laboratory

<400> SEQUENCE: 356
gagctaagct g 11

<210> SEQ ID NO 357
<211> LENGTH: 11
<212> TYPE: DNA
<213> ORGANISM: Artificial Sequence
<220> FEATURE:
<223> OTHER INFORMATION: made in laboratory

<400> SEQUENCE: 357
cagcttagct t 11

<210> SEQ ID NO 358
<211> LENGTH: 11
<212> TYPE: DNA
<213> ORGANISM: Artificial Sequence
<220> FEATURE:
<223> OTHER INFORMATION: made in laboratory

<400> SEQUENCE: 358
aagctaagct g 11

<210> SEQ ID NO 359
<211> LENGTH: 11
<212> TYPE: DNA
<213> ORGANISM: Artificial Sequence
<220> FEATURE:
<223> OTHER INFORMATION: made in laboratory

<400> SEQUENCE: 359
tagctaagct a 11

<210> SEQ ID NO 360
<211> LENGTH: 11
<212> TYPE: DNA
<213> ORGANISM: Artificial Sequence
<220> FEATURE:
<223> OTHER INFORMATION: made in laboratory

<400> SEQUENCE: 360
tagcttagct a 11

<210> SEQ ID NO 361
<211> LENGTH: 11
<212> TYPE: DNA
<213> ORGANISM: Artificial Sequence
<220> FEATURE:
<223> OTHER INFORMATION: made in laboratory

<400> SEQUENCE: 361
tagctaagct g 11

<210> SEQ ID NO 362
<211> LENGTH: 11
<212> TYPE: DNA
<213> ORGANISM: Artificial Sequence
<220> FEATURE:
<223> OTHER INFORMATION: made in laboratory

<400> SEQUENCE: 362
cagcttagct a 11

<210> SEQ ID NO 363
<211> LENGTH: 11
<212> TYPE: DNA
<213> ORGANISM: Artificial Sequence
<220> FEATURE:
<223> OTHER INFORMATION: made in laboratory

<400> SEQUENCE: 363
tagctaagct c 11

<210> SEQ ID NO 364
<211> LENGTH: 11
<212> TYPE: DNA
<213> ORGANISM: Artificial Sequence
<220> FEATURE:
<223> OTHER INFORMATION: made in laboratory

<400> SEQUENCE: 364
gagcttagct a 11

<210> SEQ ID NO 365
<211> LENGTH: 11
<212> TYPE: DNA
<213> ORGANISM: Artificial Sequence
<220> FEATURE:
<223> OTHER INFORMATION: made in laboratory

<400> SEQUENCE: 365
tagctaagct t 11

<210> SEQ ID NO 366
<211> LENGTH: 11
<212> TYPE: DNA
<213> ORGANISM: Artificial Sequence
<220> FEATURE:
<223> OTHER INFORMATION: made in laboratory

<400> SEQUENCE: 366
aagcttagct a 11

<210> SEQ ID NO 367
<211> LENGTH: 11
<212> TYPE: DNA
<213> ORGANISM: Artificial Sequence
<220> FEATURE:
<223> OTHER INFORMATION: made in laboratory

<400> SEQUENCE: 367
tagctgagct a 11

<210> SEQ ID NO 368
<211> LENGTH: 11
<212> TYPE: DNA

<213> ORGANISM: Artificial Sequence
<220> FEATURE:
<223> OTHER INFORMATION: made in laboratory

<400> SEQUENCE: 368
tagctcagct a 11

<210> SEQ ID NO 369
<211> LENGTH: 11
<212> TYPE: DNA
<213> ORGANISM: Artificial Sequence
<220> FEATURE:
<223> OTHER INFORMATION: made in laboratory

<400> SEQUENCE: 369
tagctgagct g 11

<210> SEQ ID NO 370
<211> LENGTH: 11
<212> TYPE: DNA
<213> ORGANISM: Artificial Sequence
<220> FEATURE:
<223> OTHER INFORMATION: made in laboratory

<400> SEQUENCE: 370
cagctcagct a 11

<210> SEQ ID NO 371
<211> LENGTH: 11
<212> TYPE: DNA
<213> ORGANISM: Artificial Sequence
<220> FEATURE:
<223> OTHER INFORMATION: made in laboratory

<400> SEQUENCE: 371
tagctgagct c 11

<210> SEQ ID NO 372
<211> LENGTH: 11
<212> TYPE: DNA
<213> ORGANISM: Artificial Sequence
<220> FEATURE:
<223> OTHER INFORMATION: made in laboratory

<400> SEQUENCE: 372
gagctcagct a 11

<210> SEQ ID NO 373
<211> LENGTH: 11
<212> TYPE: DNA
<213> ORGANISM: Artificial Sequence
<220> FEATURE:
<223> OTHER INFORMATION: made in laboratory

<400> SEQUENCE: 373
tagctgagct t 11

<210> SEQ ID NO 374
<211> LENGTH: 11
<212> TYPE: DNA
<213> ORGANISM: Artificial Sequence
<220> FEATURE:
<223> OTHER INFORMATION: made in laboratory

<400> SEQUENCE: 374
aagctcagct a 11

<210> SEQ ID NO 375
<211> LENGTH: 11
<212> TYPE: DNA
<213> ORGANISM: Artificial Sequence
<220> FEATURE:
<223> OTHER INFORMATION: made in laboratory

<400> SEQUENCE: 375
tagctcagct a 11

<210> SEQ ID NO 376
<211> LENGTH: 11
<212> TYPE: DNA
<213> ORGANISM: Artificial Sequence
<220> FEATURE:
<223> OTHER INFORMATION: made in laboratory

<400> SEQUENCE: 376
tagctgagct a 11

<210> SEQ ID NO 377
<211> LENGTH: 11
<212> TYPE: DNA
<213> ORGANISM: Artificial Sequence
<220> FEATURE:
<223> OTHER INFORMATION: made in laboratory

<400> SEQUENCE: 377
tagctcagct g 11

<210> SEQ ID NO 378
<211> LENGTH: 11
<212> TYPE: DNA
<213> ORGANISM: Artificial Sequence
<220> FEATURE:
<223> OTHER INFORMATION: made in laboratory

<400> SEQUENCE: 378
cagctgagct a 11

<210> SEQ ID NO 379
<211> LENGTH: 11
<212> TYPE: DNA
<213> ORGANISM: Artificial Sequence
<220> FEATURE:
<223> OTHER INFORMATION: made in laboratory

<400> SEQUENCE: 379
tagctcagct c 11

<210> SEQ ID NO 380
<211> LENGTH: 11
<212> TYPE: DNA
<213> ORGANISM: Artificial Sequence
<220> FEATURE:
<223> OTHER INFORMATION: made in laboratory

<400> SEQUENCE: 380
gagctgagct a 11

<210> SEQ ID NO 381
<211> LENGTH: 11
<212> TYPE: DNA
<213> ORGANISM: Artificial Sequence
<220> FEATURE:

<223> OTHER INFORMATION: made in laboratory

<400> SEQUENCE: 381
tagctcagct t 11

<210> SEQ ID NO 382
<211> LENGTH: 11
<212> TYPE: DNA
<213> ORGANISM: Artificial Sequence
<220> FEATURE:
<223> OTHER INFORMATION: made in laboratory

<400> SEQUENCE: 382
aagctgagct a 11

<210> SEQ ID NO 383
<211> LENGTH: 11
<212> TYPE: DNA
<213> ORGANISM: Artificial Sequence
<220> FEATURE:
<223> OTHER INFORMATION: made in laboratory

<400> SEQUENCE: 383
tagcttagct a 11

<210> SEQ ID NO 384
<211> LENGTH: 11
<212> TYPE: DNA
<213> ORGANISM: Artificial Sequence
<220> FEATURE:
<223> OTHER INFORMATION: made in laboratory

<400> SEQUENCE: 384
tagctaagct a 11

<210> SEQ ID NO 385
<211> LENGTH: 11
<212> TYPE: DNA
<213> ORGANISM: Artificial Sequence
<220> FEATURE:
<223> OTHER INFORMATION: made in laboratory

<400> SEQUENCE: 385
tagcttagct g 11

<210> SEQ ID NO 386
<211> LENGTH: 11
<212> TYPE: DNA
<213> ORGANISM: Artificial Sequence
<220> FEATURE:
<223> OTHER INFORMATION: made in laboratory

<400> SEQUENCE: 386
cagctaagct a 11

<210> SEQ ID NO 387
<211> LENGTH: 11
<212> TYPE: DNA
<213> ORGANISM: Artificial Sequence
<220> FEATURE:
<223> OTHER INFORMATION: made in laboratory

<400> SEQUENCE: 387
tagcttagct c 11

-continued

```
<210> SEQ ID NO 388
<211> LENGTH: 11
<212> TYPE: DNA
<213> ORGANISM: Artificial Sequence
<220> FEATURE:
<223> OTHER INFORMATION: made in laboratory

<400> SEQUENCE: 388

gagctaagct a                                                          11


<210> SEQ ID NO 389
<211> LENGTH: 11
<212> TYPE: DNA
<213> ORGANISM: Artificial Sequence
<220> FEATURE:
<223> OTHER INFORMATION: made in laboratory

<400> SEQUENCE: 389

tagcttagct t                                                          11


<210> SEQ ID NO 390
<211> LENGTH: 11
<212> TYPE: DNA
<213> ORGANISM: Artificial Sequence
<220> FEATURE:
<223> OTHER INFORMATION: made in laboratory

<400> SEQUENCE: 390

aagctaagct a                                                          11
```

UMI AND APPLICATION THEREOF, MOLECULAR IDENTIFIER GROUP, ADAPTER, ADAPTER LIGATION REAGENT, KITS, METHOD FOR CONSTRUCTING DNA LIBRARY AND METHOD FOR SEQUENCING GENE

CROSS-REFERENCE TO RELATED APPLICATION

This application is a national phase entry under 35 USC 371 of International Patent Application No. PCT/CN2021/134159 filed on Nov. 29, 2021, which is incorporated herein by reference in its entirety.

TECHNICAL FIELD

The present disclosure relates to the field of biotechnologies, and in particular, to a UMI and an application thereof, a molecular identifier group, an adapter, an adapter ligation reagent, kits, a method for constructing a DNA library and a method for sequencing a gene.

BACKGROUND

Next generation sequencing (NGS, also referred to as second generation sequencing) technologies are currently most widely used sequencing technologies, which have advantages of high sequencing depth, large throughput, high accuracy and good sensitivity.

SUMMARY

In one aspect, a unique molecular identifier (UMI) is provided. The UMI includes: at least one random base and at least one fixed base.

In some embodiments, the at least one random base includes a plurality of random bases, and/or the at least one fixed base includes a plurality of fixed bases. The plurality of random bases and/or the plurality of fixed bases are arranged consecutively: or at least two random bases of the plurality of random bases are arranged at intervals, and/or at least two fixed bases of the plurality of fixed bases are arranged at intervals.

In some embodiments, in a case where the at least one random base includes the plurality of random bases, and the at least two random bases of the plurality of random bases are arranged at intervals, every two random bases arranged at intervals are separated by one to five fixed bases.

In some embodiments, the at least one random base includes at least three random bases. Every two of the at least three random bases are arranged at intervals from each other and separated by a group of fixed bases, and every two groups of fixed bases each include a same number of fixed bases.

In some embodiments, for the every two adjacent groups of fixed bases, at least one fixed base of one group of fixed bases is different from a fixed base of another group of fixed bases.

In some embodiments, the every two random bases arranged at intervals are separated by 2 to 4 fixed bases, and the 2 to 4 fixed bases are different from each other.

In some embodiments, the at least one random base includes three random bases.

In some embodiments, the UMI includes 7 to 11 bases.

In another aspect, a molecular identifier group is provided. The molecular identifier group includes: two unique molecular identifiers (UMIs) binding to each other through complementary pairing of at least a portion of bases thereof. At least one UMI is the UMI described above.

In yet another aspect, an adapter is provided. The adapter includes: a first strand, a second strand and at least one unique molecular identifier (UMI). Each UMI is located on the first strand or the second strand. The at least one UMI is the UMI described above.

In some embodiments, the at least one UMI includes two UMIs. The two UMI are respectively located on the first strand and the second strand, and bind to each other through complementary pairing of at least a portion of bases thereof.

In some embodiments, the first strand is a forward strand, and the second strand is a reverse strand. The first strand includes a first sequencing primer sequence. The second strand includes a second sequencing primer sequence. A UMI located on the first strand is located downstream of the first sequencing primer sequence. A UMI located on the second strand is located upstream of the second sequencing primer sequence.

In yet another aspect, an adapter ligation reagent is provided. The adapter ligation reagent includes a plurality of kinds of adapters. The plurality of kinds of adapters are each the adapter as described above. Of the plurality of kinds of adapters, for every two kinds of adapters, at least one random base of at least one UMI included in one kind of adapter is different from at least one random base of at least one UMI included in another kind of adapter.

In yet another aspect, a kit is provided. The kit includes: the adapter ligation reagent described above.

In yet another aspect, an application of unique molecular identifiers (UMIs) described above in sequencing a gene is provided.

In some embodiments, the gene includes a deoxyribonucleic acid (DNA) molecule for expressing genetic information. The UMIs are configured to label different DNA molecules.

In yet another aspect, a method for constructing a deoxyribonucleic acid (DNA) library is provided. The method includes:

- obtaining fragmented DNA; performing end repair and adenine (A) addition on the fragmented DNA to obtain end-repaired products; treating the end-repaired products with the adapter ligation reagent described above, so as to make the adapters of the adapter ligation reagent react with the end-repaired products to obtain adapter ligation products; and enriching the adapter ligation products to obtain the DNA library.

In yet another aspect, a method for sequencing a gene is provided. The method includes: performing gene sequencing on deoxyribonucleic acid (DNA) by using the DNA library obtained by the method for constructing the DNA library described above.

In yet another aspect, a kit is provided. The kit includes: the DNA library obtained by the method for constructing the DNA library described above.

BRIEF DESCRIPTION OF THE DRAWINGS

In order to describe technical solutions in the present disclosure more clearly, accompanying drawings to be used in some embodiments of the present disclosure will be introduced briefly below. However, the accompanying drawings to be described below are merely accompanying drawings of some embodiments of the present disclosure, and a person having ordinary skill in the art can obtain other drawings according to these accompanying drawings. In addition, the accompanying drawings in the following description may be regarded as schematic diagrams, but are not limitations on an actual size of a product, an actual process of a method and an actual timing of a signal involved in the embodiments of the present disclosure.

DETAILED DESCRIPTION

Figure 1:
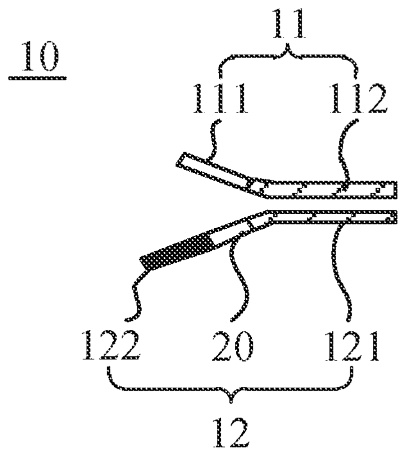
FIG. 1 is a structural diagram of a Y-shaped adapter, in accordance with some embodiments.

Technical solutions in some embodiments of the present disclosure will be described clearly and completely below with reference to the accompanying drawings. However, the described embodiments are merely some but not all embodiments of the present disclosure. All other embodiments obtained by a person of ordinary skill in the art based on the embodiments of the present disclosure shall be included in the protection scope of the present disclosure.

Unless the context requires otherwise, throughout the description and the claims, the term "comprise" and other forms thereof such as the third-person singular form "comprises" and the present participle form "comprising" are construed as an open and inclusive meaning, i.e., "including, but not limited to". In the description of the specification, the terms such as "one embodiment", "some embodiments", "exemplary embodiments", "example", "specific example" or "some examples" are intended to indicate that specific features, structures, materials or characteristics related to the embodiment(s) or example(s) are included in at least one embodiment or example of the present disclosure. Schematic representation of the above terms does not necessarily refer to the same embodiment(s) or examples(s). In addition, the specific features, structures, materials or characteristics may be included in any one or more embodiments or examples in any suitable manner.

Hereinafter, the terms such as "first" and "second" are used for descriptive purposes only, but are not to be construed as indicating or implying the relative importance or implicitly indicating the number of indicated technical features. Thus, the features defined with "first" and "second" may explicitly or implicitly include one or more of the features. In the description of the embodiments of the present disclosure, the term "a plurality of/the plurality of" means two or more unless otherwise specified.

The phrase "at least one of A, B and C" has a same meaning as the phrase "at least one of A, B or C", and they both include the following combinations of A, B and C: only A, only B, only C, a combination of A and B, a combination of A and C, a combination of B and C, and a combination of A, B and C.

The phrase "A and/or B" includes the following three combinations: only A, only B, and a combination of A and B.

The phrase "applicable to" or "configured to" as used herein indicates an open and inclusive expression, which does not exclude devices that are applicable to or configured to perform additional tasks or steps.

As used herein, the term "DNA" is an abbreviation for deoxyribonucleic acid. DNA, as a carrier of genetic information in biological cells, is mainly used to guide synthesis of RNA and proteins in a body. The DNA is a macromolecular polymer composed of deoxynucleotides. The deoxynucleotide is composed of a phosphate, a deoxyribose and a base. There are four main kinds of bases, i.e., adenine (A), guanine (G), cytosine (C) and thymine (T).

As used herein, the term "RNA" is an abbreviation for ribonucleic acid. The RNA, as a carrier of genetic information that exists in biological cells and some viruses and viroids, is mainly used to guide synthesis of proteins in the body. The RNA is a macromolecular polymer composed of ribonucleotides. A ribonucleotide is composed of a phosphate, a ribose and a base. There are four main kinds of bases, i.e., adenine (A), guanine (G), cytosine (C) and uracil (U).

At present, next-generation sequencing technologies are widely used in reproductive genetics, tumor detection and other fields, especially in liquid biopsy. In a process of preparing a library for liquid biopsy, a replication of a polymerase chain reaction (PCR) amplification enzyme has a certain base error rate. In addition, an error rate of a sequencer in reading bases is in a range of 0.01% to 0.1% (that is, there are 1 to 10 erroneous bases in every 1000 bases) during a sequencing process. Such noise mutations (also referred to as non-native mutations) appear in samples with low frequency mutations or ultra-low frequency mutations, which makes it difficult to determine whether mutations at frequencies of 1% or less are genuine gene mutations or noisy mutations caused by sequencing or PCR errors. A detection of these low frequency mutations is significant, so that unique molecular identifiers (UMIs), which are also referred to as molecular barcodes, are introduced into original DNA fragments. A principle of the detection is to add a unique identifier sequence to each original DNA fragment, and the identifier sequence will be sequenced together with the original DNA fragment after library construction and PCR amplification. In this way, according to different identifier sequences, it may be possible to distinguish between DNA templates (referred to as DNA molecules below) from different sources from each other, and determine which are false positive mutations caused by random errors during PCR amplification and sequencing and which are mutations actually carried by a patient, thereby improving detection sensitivity and specificity. UMIs label the original DNA fragments, so that different DNA molecules from different sources carry different molecular identifiers; when sequencing results are analyzed, same inserts (i.e., the original DNA fragments) are screened out; if two ends of a same insert have complementary paired UMI adapters, the UMI adapters may be used to mark forward and reverse strands (a forward strand and a reverse strand) of the same insert; and if mutant bases appear at a same position in both the forward and reverse strands, such a mutation is marked as a real mutation. In this way, an original mutation state is restored.

At present, there are two main strategies for introducing the UMIs. A first strategy is to introduce single-ended UMIs. For example, eight random bases may be added to a P5 end of an adapter instead of an Index. Adapters synthesized in this way have advantages such as simplicity, economy and applicability, which have been widely used. However, in a process of constructing a library, bindings of UMI adapters are random, which causes that a single original DNA fragment binds with two different UMI adapters, and that a forward strand and a reverse strand bind with different UMIs. Consequently, information of the original forward and reverse strands cannot be tracked, and then forward and reverse strand sequences cannot be corrected accurately. In addition, if there is a base mutation in a UMI sequence, a number of bases in the original DNA fragment will increase, resulting in introduction of potential false positive mutations. A second strategy is to introduce double-ended UMIs. That is, in related art, a single-strand adapter (a sequence) is firstly synthesized, the single-strand adapter (the sequence) including a first sequence and a second sequence, the second sequence including protection bases of a restriction endonuclease and a double-stranded molecular identifier of random-bases; and then, a double-strand adapter is formed by annealing the single-strand adapter sequence; and finally, an adapter with a 3'-dT tail may be obtained by enzyme cleavage. Although such a double-strand adapter may effectively solve a problem that the single-ended UMIs cannot track the original forward and reverse strands, false positive mutations will still be introduced when a UMI sequence itself is mutated.

Some embodiments of the present disclosure provide an adapter 10. As shown in FIG. 1, the adapter 10 includes: a first strand 11, a second strand 12 and at least one UMI 20. Each UMI 20 is located on the first strand 11 or on the second strand 12.

Considering an example where adapters 10 are Y-shaped adapters, the adapters may be classified into long adapters (complete Y-shaped adapters) and short adapters (incomplete Y-shaped adapters) according to whether the adapters 10 can match a PCR-free library. The long adapter binds to both ends of a DNA fragment to be sequenced (i.e., the original DNA fragment described above) by TA ligation, and if a library yield is sufficient, sequencing on a computer may be directly performed without PCR amplification; while after the short adapter binds to the both ends of the DNA fragment by TA ligation, PCR amplification must be firstly performed by using indexing primers complementary to the short adapter to form a complete adapter before sequencing on the computer is performed. Such a difference between the short adapter and the long adapter is mainly caused by different manners of introducing Index sequences of the short adapters and the long adapters. The Index sequence is configured to label samples of different sequences to be tested. A single sample may include tens of thousands of DNA molecules, and UMIs 20 are used to label different DNA molecules in a same sample or in different samples.

Considering an example where the adapters 10 are the long adapters, the adapters 10 may be classified into single-ended index adapters and double-ended index adapters. The single-ended index adapter only has an Index sequence at a P7 end, and the double-ended index adapter has Index sequences at both a P5 end and the P7 end.

Here, considering an example where the adapter 10 is a single-ended Index adapter, in a case where the adapter 10 includes one UMI 20, as shown in FIG. 1, the UMI 20 may be added at the P7 end to replace an Index sequence. In this case, the first strand 11 may include a first PCR amplification primer 111 (i.e., commonly referred to as P5) and a first sequencing primer sequence 112 (R1 SP) sequentially arranged from a 5' end; the second strand 12 may include a second sequencing primer sequence 121 (R2 SP), the UMI 20 and a second PCR amplification primer 122 (i.e., commonly referred to as P7). That is, the adapter 10 is a single-ended UMI adapter.

In some embodiments, the at least one UMI 20 includes at least one random base and at least one fixed base.

In a single UMI 20, numbers of random base(s) and fixed base(s) and a manner in which the random base(s) and the fixed base(s) are not specifically limited.

In some embodiments, considering an example where there are one random base and one fixed base, the random base and the fixed base may be arranged in sequence in a same direction. For example, the random base and the fixed base are sequentially arranged in a direction from a 5' end to a 3' end of the UMI sequence; alternatively, the random base and the fixed base are sequentially arranged from the 3' end to the 5' end of the UMI sequence.

In some other embodiments, considering an example where there are a plurality of random bases and/or a plurality of fixed bases, there are two possible cases.

In a first case, there are the plurality of random bases and/or the plurality of fixed bases, and the plurality of random bases and/or the plurality of fixed bases are arranged consecutively.

In this case, depending on whether there is one random base or there are the plurality of random bases, and whether there is one fixed base or there are the plurality of fixed bases, there are many possible situations. In a first situation, there are the plurality of random bases and the one fixed base. In this situation, the plurality of random bases are arranged consecutively. In this situation, the fixed base may be located on a side of the plurality of random bases (e.g., a direction from the 5' end to the 3' end of the UMI sequence is referred to as a first direction, and a direction from the 5' end of the UMI sequence to the 3' end is referred to as a second direction, and the fixed base may be located on a side of the plurality of random bases in the first direction or in the second direction). In a second situation, there are the plurality of fixed bases and the one random base. In this situation, the random base may be located on a side of the plurality of fixed bases (e.g., the direction from the 5' end to the 3 end of the UMI sequence is referred to as the first direction, the direction from the 5' end of the UMI sequence to the 3' end is referred to as the second direction, and the random base may be located on a side of the plurality of fixed bases in the first direction or in the second direction). In a third situation, there are the plurality of random bases and the plurality of fixed bases. In this situation, the plurality of random bases and the plurality of fixed bases are both arranged consecutively. In this situation, the plurality of fixed bases may be located in a side of the plurality of random bases (e.g., the direction from the 5' end to the 3' end of the UMI sequence is referred to as the first direction, the direction from the 5' end of the UMI sequence to the 3' end is referred to as the second direction, and the plurality of fixed bases may be located on a side of the plurality of random bases in the first direction or in the second direction).

In a second case, there are the plurality of random bases and/or the plurality of fixed bases, and at least two random bases of the plurality of random bases and/or at least two fixed bases of the plurality of fixed bases are arranged at intervals.

In this case, depending on whether there is one random base or there are the plurality of random bases and whether there is one fixed base or there are the plurality of fixed bases, there are many possible situations. In a first situation, there are the plurality of random bases and the one fixed base. In this situation, the fixed base is located between any two adjacent random bases of the plurality of random bases. In a second situation, there are the plurality of fixed bases and the one random base. In this situation, the random base is located between any two adjacent fixed bases of the plurality of fixed bases. In a third situation, there are the plurality of random bases and the plurality of fixed bases. In this situation, there are a plurality of possible arrangements. In a first arrangement, at least two random bases of the plurality of random bases are arranged at intervals, and the plurality of fixed bases are located between any two random bases arranged at intervals. In a second arrangement, at least two fixed bases of the plurality of fixed bases are arranged at intervals, and the plurality of random bases are located between any two fixed bases arranged at intervals. In a third arrangement, at least two random bases of the plurality of random bases are arranged at intervals, and at least two fixed bases of the plurality of fixed bases are arranged at intervals. That is, at least two bases of the plurality of random bases are arranged at intervals and at least two bases of the plurality of fixed bases are arranged at intervals. There may be one or more fixed bases between two random bases arranged at intervals, and there may also be one or more random bases between two fixed bases arranged at intervals.

Considering an example where there are the plurality of random bases and the at least two random bases of the plurality of random bases are arranged at intervals, every two random bases arranged at intervals may be separated by 1 to 5 fixed bases.

It will be noted that, the "random base", just as its name implies, means that the base is random, which may be any one selected randomly from the four bases (A, T, C and G), and may be represented by N. Random bases are selected from different bases, and may be used to label different DNA molecules.

For example, considering an example where there is one random base in a single UMI 20, the N in the UMI 20 may be any one selected from the four bases. In this case, according to different Ns in UMIs 20, there may be four kinds of UMIs. The four kinds of UMIs 20 may be formed into $4^2$ (i.e. 16) adapters (a single DNA molecule binds with two adapters), so that $4^2$ (i.e., 16) different DNA molecules may be labeled to detect the $4^2$ (i.e., 16) different DNA molecules.

Considering an example where there are three random bases in a single UMI 20, each N in the UMI 20 may be any one selected from the four bases. Since the three Ns has $4^3$ (i.e., 64) combinations, there may be $4^3$ kinds (i.e., 64) of UMIs 20. The 64 kinds of UMIs 20 may be formed into $64^2$ (i.e., 4096) kinds of adapters (a single DNA molecule binds with two adapters), so that $64^2$ (i.e., 4096) different DNA molecules may be labeled to detect of the $64^2$ (i.e., 4096) different DNA molecules.

It will be seen that, as the larger the number of random bases is, the more kinds of UMIs there are, and then the larger the number of DNA molecules that can be labeled becomes.

The fixed bases are selected from known fixed bases, and used for correcting a sequence to be tested and the UMI when the two have errors during amplification or sequencing, which reduces the introduction of false positive mutations.

Figure 2:
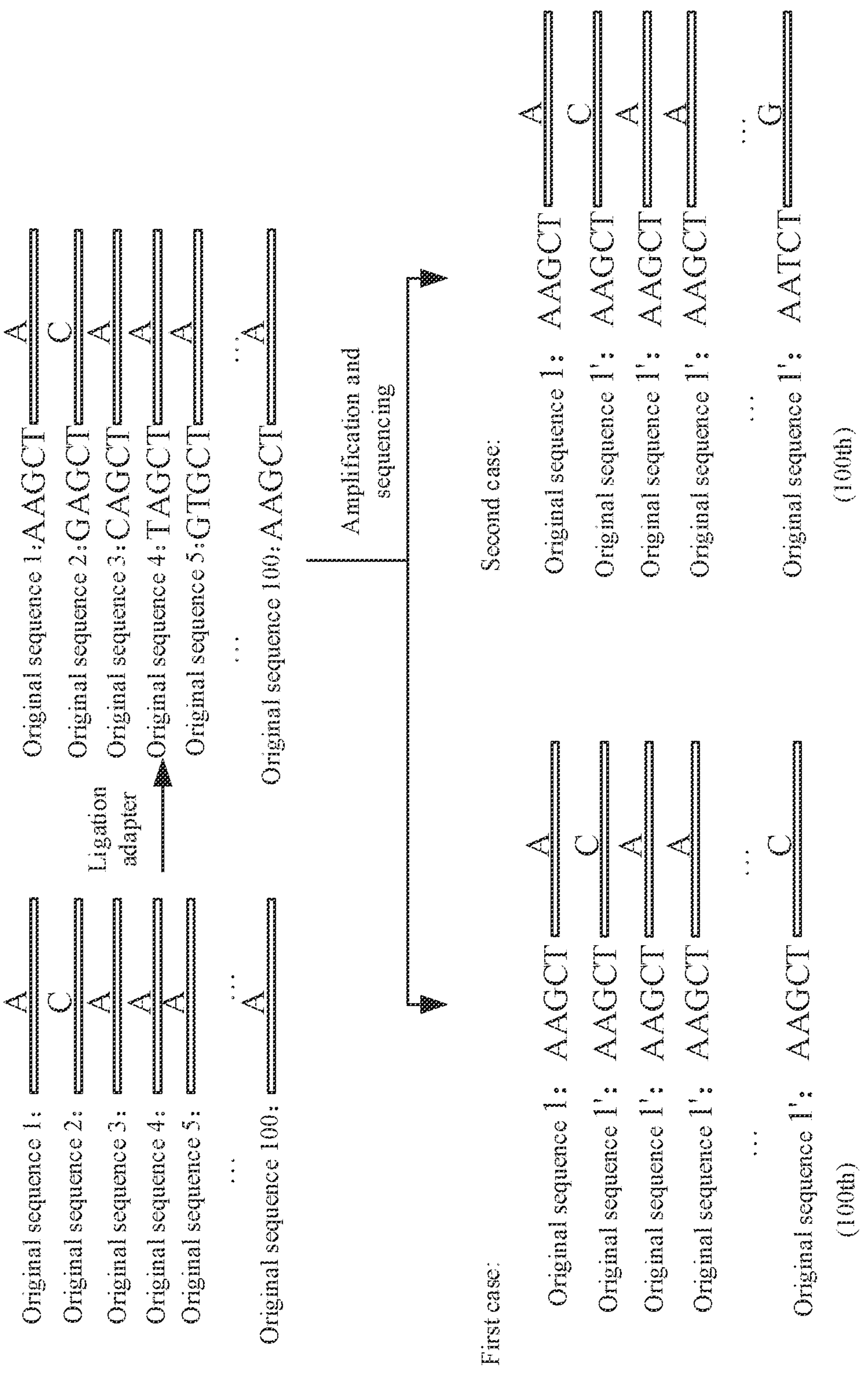
FIG. 2 is a flowchart of a sequencing method, in accordance with some embodiments.

As shown in FIG. 2, considering an example where there are 100 original DNA fragments with a same starting position and a same ending position (i.e., a same sequence), the 100 original DNA fragments being recorded as an original sequence 1, an original sequence 2, an original sequence 3, . . . an original sequence 99 and an original sequence 100, where the original sequence 2 is a mutated sequence, and a real mutation frequency is 1% as an example. The original DNA fragments each bind with a different UMI adapter to obtain sequences corresponding to the original sequence 1 to the original sequence 100 which are still recorded as the original sequence 1, the original sequence 2, the original sequence 3, . . . the original sequence 99 and the original sequence 100.

The 100 original sequences binding with UMI adapters are amplified by PCR and enriched to obtain a DNA library including 100 original sequences binding with the UMI adapters (for distinction, the remaining 99 original sequences binding with UMI adapters that are obtained by copying are recorded as original sequences 1'). As shown in a first case in FIG. 2, for the original sequences 1, the 99 original sequences 1' binding with the UMI adapters which are copied by PCR amplification may be determined according to AAGCT on the UMI adapters. Since a detection site of the original sequence 1 is a base A, theoretically, detection sites of the 99 original sequences 1' obtained by copying should also be bases As. However, if a corresponding detection site of a 100th original sequence 1' has a base C, it may be determined that it is a noise mutation caused by PCR amplification error or sequencing error. However, in a case where a DNA sequence and a UMI adapter of the 100th original sequence 1' both have amplification errors, if the UMI is a molecular identifier composed of random bases, the DNA sequence and the UMI adapter will both be determined to be real mutations, and thus false positive mutations are introduced. In the embodiments of the present disclosure, as in a second case in FIG. 2, since a middle base in the UMI 20 with five bases is always a base G, it is determined that the UMI of the 100th original sequence 1' is also a noise mutation caused by PCR amplification or sequencing according to that the five bases in the UMI 20 are AAGCT but not AATCT in the remaining original sequences; and it is also determined that the DNA sequence of the 100th original sequence 1' is also a noise mutation caused by PCR amplification or sequencing according to that DNA sequences of the remaining 99 original sequences1' labeled by the UMIs each with five bases 20 have no mutations.

It will be seen that, by using a UMI 20 partially composed of fixed base(s), it may be possible to ensure diversity of the adapters to label different original DNA fragments; and moreover, noise mutations introduced by PCR amplification or sequencing may be avoided to a certain extent, which improves detection accuracy.

In some embodiments of the present disclosure, there are at least three random bases, the at least three random bases are arranged at intervals from each other, every two random bases arranged at intervals are separated by a group of fixed bases, and every two groups of fixed bases each include a same number of fixed bases.

In these embodiments, by limiting the number of the random bases to at least three, it may be possible to ensured that at least 4096 different DNA molecules are labeled by the UMIs 20, which increases a number of molecules to be tested, thereby improving the detection accuracy of samples. In addition, by providing a group of fixed bases between every two random bases arranged at intervals and setting the every two groups of fixed bases each to include the same number of fixed bases, it may be possible to improve arrangement regularity of the random bases and the fixed bases, so that it is easy to determine whether a mutation is a mutation of the fixed base or a mutation of an original DNA fragment itself, and then reduces the introduction of false positive mutations and improves the detection accuracy. In addition, it is found through testing that, under a premise of a same number of bases in the UMIs 20, detection accuracy in a case where every two random bases of the plurality of random bases are arranged at intervals from each other is higher than a case where the plurality of random bases are consecutively arranged.

In some other embodiments, since the fixed bases play a role of excluding noise mutations introduced by PCR amplification or sequencing, the larger the number of the fixed bases in a single UMI 20, the better an error tolerance during detection, and then the more accurate the detection. Here, considering an example where the UMI 20 includes three random bases and four fixed bases, there are the four fixed bases in the UMI 20 for error tolerance in a subsequent sequencing, so that an error tolerance rate may be 4 divided by 7 times 100%, i.e., about 57%.

However, considering that an amount of data to be tested will be occupied as the number of the fixed bases increases, it is not that the fixed base the more the better.

In light of this, in some embodiments, every two random bases arranged at intervals are separated from each other by two to four fixed bases.

In these embodiments, by providing two to four fixed bases between every two random bases, an occupation of the data to be tested due to an excessive number of fixed bases may be avoided while the error tolerance rate of detection is ensured.

The two to four fixed bases may be same or different, which are not specifically limited here.

In some embodiments, the two to four fixed bases are different from each other.

In these embodiments, since the two to four fixed bases are different from each other, it may be possible to avoid an concentration of a same kind of fluorescence (labeling a same kind of bases) during sequencing (the same kind of bases are prone to the concentration of the same kind of fluorescence), thereby preventing a problem of inaccurate reading due to the concentration of the fluorescence, which improves the detection accuracy.

In some other embodiments, for every two adjacent groups of fixed bases, at least one fixed base of one group of fixed bases is different from a fixed base of the other group of fixed bases.

For example, considering an example where there are three random bases in a single UMI 20, the three random bases are arranged at intervals from each other, and every two random bases are separated by one fixed base (i.e., every two adjacent groups of fixed bases each including one fixed base), since for every two adjacent groups of fixed bases, at least one fixed base of one group of fixed bases is different from a fixed base of the other group of fixed bases, a sequence of the UMI may be represented as follows:

NN1NN2N, where N1 and N2 are different from each other, and are each any one independently selected from A, T, C and G; and the three Ns may be same or different, and are each any one independently selected from A, T, C and G.

That is, considering an example where N1 is A and N2 is C, two adjacent group of fixed bases are respectively A and C which are different from each other.

Compared with N1 and N2 that are a same kind of base, it may be possible to avoid the concentration of the same kind of fluorescence (labeling the same kind of bases) during sequencing (the same kind of bases are prone to the concentration of the same kind of fluorescence), thereby preventing the problem of inaccurate reading due to the concentration of the fluorescence, which improves the detection accuracy.

For still another example, considering an example where there are three random bases in a single UMI 20, the three random bases are arranged at intervals from each other, and every two random bases are separated by two fixed base (i.e., every two adjacent groups of fixed bases each including two fixed base), since for every two adjacent groups of fixed bases, at least one fixed base of one group of fixed bases is different from a fixed base of the other group of fixed bases, a sequence of the UMI may be represented as follows:

NN3N4NN5N6N, where N3 and N4 may be same or different, and are each any one independently selected from A, T, C and G; N5 and N6 are same or different, and are each any one independently selected from A, T, C and G; at least one of N3 and N4 is different from each of N5 and N6; and the three Ns are same or different, and are each any one independently selected from A, T, C and G.

In this case, according to whether N3 and N4 are the same, there may be two possible cases. In a first case, N3 and N4 are the same. In this case, there may be two possible situations according to whether N5 and N6 are the same. In a first situation, N5 and N6 are different. In this situation, at least one of the fixed bases N5 and N6 is different from a fixed base of the fixed bases N3 and N4. That is, one of the fixed bases N5 and N6 is different from each of the two fixed bases N3 and N4; or both of the two fixed bases N5 and N6 are different from each of the fixed bases N3 and N4. In a case where one of the fixed bases N5 and N6 is different from each of the two fixed bases N3 and N4, considering an example where both N3 and N4 are As, N5 and N6 may be respectively A and C, or A and G, or A and T. In a case where N5 and N6 are respectively A and C, the two adjacent groups of fixed bases are respectively AA and AC, and for the two groups of fixed bases, one fixed base (C) of one group of fixed bases is different from the two fixed bases (As) in the other group of fixed bases. In a case where N5 and N6 are respectively A and G, the two adjacent groups of fixed bases are respectively AA and AG, and for the two groups of fixed bases, one fixed base (G) in one group of fixed bases is different from the two fixed bases (As) in the other group of fixed bases. In a case where N5 and N6 are respectively A and T, the two adjacent groups of fixed bases are respectively AA and AT, and for the two groups of fixed bases, one fixed base (T) in one group of fixed bases is different from the two fixed bases (As) in the other group of fixed bases. In a case where both of the two fixed bases N5 and N6 are different from each of the fixed bases N3 and N4, still considering an example where both N3 and N4 are As, N5 and N6 may be respectively C and G, C and T, or G and T. In a case where N5 and N6 are respectively C and G, the two adjacent groups of fixed bases are respectively AA and CG, and for the two groups of fixed bases, both of the two fixed bases (C and G) in one group of fixed bases are different from the two fixed bases (As) in the other group of fixed bases. In a case where N5 and N6 are respectively C and T, the two adjacent groups of fixed bases are respectively AA and CT, and for the two groups of fixed bases, both of the two fixed bases (C and T) in one group of fixed bases are different from the two fixed bases (As) in the other group of fixed bases. In a case where N5 and N6 are respectively G and T, the two adjacent groups of fixed bases are respectively AA and GT, and for the two groups of fixed bases, both of the two fixed bases (G and T) in one group of fixed bases are also different from the two fixed bases (As) in the other group of fixed bases. In a second situation, N5 and N6 are the same. In this situation, at least one of the fixed bases N5 and N6 is different from a fixed base of the fixed bases N3 and N4. That is, both of the two fixed bases N5 and N6 are different from each of the two fixed bases N3 and N4. For example, still considering an example where both N3 and N4 are As, N5 and N6 may be both Ts, Gs or Cs. In a case where N5 and N6 are both Ts, the two fixed bases N5 and N6 (Ts) are different from the two fixed bases N3 and N4 (As). In a case where N5 and N6 are both Gs, the two fixed bases N5 and N6 (Gs) are different from the two fixed bases N3 and N4 (As). In a case where N5 and N6 are both Cs, the two fixed bases N5 and N6 (Cs) are different from the two fixed bases N3 and N4 (As).

In a second case, N3 and N4 are different. In this case, according to whether N5 and N6 are same, there may be two possible situations. In a first situation, N5 and N6 are different. In this situation, at least one of the fixed bases N5 and N6 is different from a fixed base of the fixed bases N3 and N4. That is, one of the fixed bases N5 and N6 is different from one of the fixed bases N3 and N4, or both of the two fixed bases N5 and N6 are different from each of the two fixed bases N3 and N4. In a case where one of the fixed bases N5 and N6 is different from one of the fixed bases N3 and N4, considering an example where N3 and N4 are respectively A and T, N5 and N6 may be respectively A and C, A and G, T and C, or T and G. In a case where N5 and N6 are respectively A and C, one (C) of the fixed bases N5 and N6 is different from one (T) of the fixed bases N3 and N4. In a case where N5 and N6 are respectively A and G, one (G) of the fixed bases N5 and N6 is different from one (T) of the fixed bases N3 and N4. In a case where N5 and N6 are respectively T and C, one (C) of the fixed bases N5 and N6 is different from one (T) of the fixed bases N3 and N4. In a case where N5 and N6 are respectively T and G, one (G) of the fixed bases N5 and N6 is different from one (T) of the fixed bases N3 and N4. In a case where both of the two fixed bases N5 and N6 are different from each of the two fixed bases N3 and N4, still considering an example where N3 and N4 are respectively A and T, N5 and N6 may be respectively G and C. In a case where N5 and N6 are respectively G and C, both of the two fixed bases N5 and N6 (G and C) are different from each of the two fixed bases N3 and N4 (A and T). In a second situation, N5 and N6 are the same. In this situation, at least one of the fixed bases N5 and N6 is different from a fixed base of the fixed bases N3 and N4. That is, the two fixed bases N5 and N6 are different from one or two of the fixed bases N3 and N4. For example, still considering an example where N3 and N4 are respectively A and T, N5 and N6 may be both As, Ts, Cs or Gs. In a case where N5 and N6 are both As, the two fixed bases N5 and N6 are different from one of the fixed bases N3 and N4. In a case where N5 and N6 are both Ts, the two fixed bases N5 and N6 are different from one of the fixed bases N3 and N4. In a case where N5 and N6 are both Cs, the two fixed bases N5 and N6 are different from each of the two fixed bases N3 and N4. In a case where N5 and N6 are Gs, the two fixed bases N5 and N6 are also different from each of the two fixed bases N3 and N4.

In these embodiments, similar to the above embodiments where every two random bases is separated by one fixed base (i.e., the two adjacent groups of fixed bases each include one fixed base), it is also possible to avoid the concentration of the same kind of fluorescence (labeling the same kind of bases) during sequencing (the same kind of bases are prone to the concentration of the same kind of fluorescence), thereby preventing the problem of inaccurate reading due to the concentration of the fluorescence, which improves the detection accuracy.

In some embodiments, there are three random bases.

In these embodiments, by limiting a number of the random bases to three, it may be possible to label 4096 different DNA molecules, thereby meeting application requirements.

In some embodiments, the UMI 20 includes seven to eleven bases.

In these embodiments, by limiting a number of the bases included in the UMI 20 to seven to eleven, it may be possible to avoid not only an occupation of the data to be tested due to an excessively large length of the UMIs 20 but also detrimental effects on an improvement of the error tolerance rate (e.g., caused by too few random bases) and/or on labeling of a large number of DNA molecules (e.g., caused by too few fixed bases) due to an excessively short length of the UMIs 20.

Figure 3:
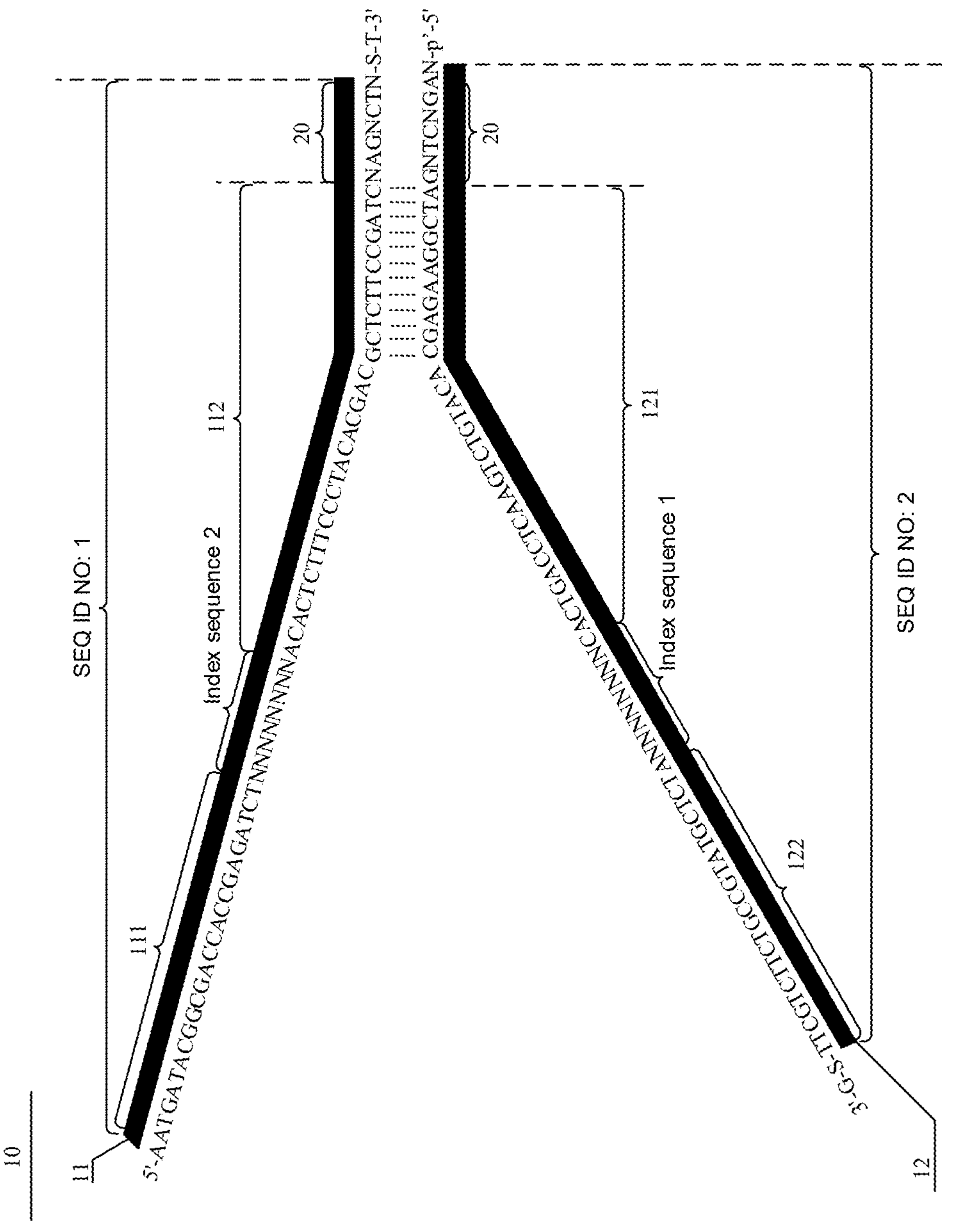
FIG. 3 is a structural diagram of another Y-shaped adapter, in accordance with some embodiments.

In some embodiments, as shown in FIG. 3, there are two UMIs 20, and the two UMIs 20 are respectively located on the first strand 11 and the second strand 12 and bind to each other through complementary pairing of at least a portion of bases thereof.

In these embodiments, the two UMIs 20 may be a first UMI and a second UMI, respectively. In this case, there are two possible situations. In a first situation, the first UMI 20 may be located between a first sequencing primer sequence 111 and a first amplification primer sequence 112. The second UMI 20 may be located between a second sequencing primer sequence and 121 a second amplification primer sequence 122. The two UMIs 20 bind to each other through complementary pairing of at least a portion of bases thereof. In this situation, the adapter 10 is same as a single-ended UMI adapter, which cannot track forward and reverse strands. In a second situation, as shown in FIG. 3, the first strand 11 is a forward strand (e.g., a chain whose 5' end and 3' end are arranged from left to right as shown in FIG. 3), and the second strand 12 is a reverse strand (e.g., a chain whose 3' end and 5' end are arranged from left to right as shown in FIG. 3), a UMI 20 located on the first strand 11 (i.e., the first UMI molecular tag) is located downstream of the first sequencing primer sequence 112, and a UMI 20 located on the second strand 12 (i.e., the second UMI molecular tag) is located upstream of the second sequencing primer sequence 121. In this situation, the first UMI and the second UMI bind to each other through complementary pairing of all of the bases thereof, and the adapter 10 may also be referred to as a double-ended UMI adapter. Compared with a single-ended UMI adapter, the adapter 10 may further track forward and reverse strands of a sequence to be tested simultaneously, so that it may be possible to mark a real mutation in a case where mutated bases at a same position on both the forward and reverse strands appear, which may further improve the detection accuracy.

In some embodiments, as shown in FIG. 3, the adapter 10 further includes an Index sequence 1 and an Index sequence 2. The Index sequence 1 is located on the second strand 12. The Index sequence 2 is located on the first strand 11. The Index sequence 1 and the Index sequence 2 may label different samples.

Some embodiments of the present disclosure provide an adapter ligation reagent. The adapter ligation reagent includes: a plurality of kinds of adapters 10, ligases, a buffer, etc. The plurality of kinds of adapters 10 are adapters 10 each as described above. The ligases may be, for example, DNA ligases or RNA ligases, and are used to promote a ligation of the plurality of kinds of adapters 10 and end repaired DNA fragments. The buffer provides a stable pH environment with for an adapter ligation reaction. Of the plurality of kinds of adapters, for every two kinds of adapters 10, at least one UMI 20 included in one kind of adapter 10 has at least one random base that is different from at least one random base of at least one UMI 20 included in another kind of adapter 10.

In these embodiments, the plurality of kinds of adapters 10 are all UMI adapters. At least one UMI 20 included in the UMI adapter includes at least one random base and at least one fixed base. Random bases corresponding to the plurality kinds of adapters are selected from different bases, so that different DNA molecules may be labeled through the different UMI adapters to realize a sequencing of the plurality of different DNA molecules. Fixed bases are selected from the known fixed bases, so that the sequence to be tested and the UMI may be corrected when the two themselves have errors during amplification or sequencing, which reduces the introduction of false positive mutations.

Some embodiments of the present disclosure provide a kit. The kit includes the adapter ligation reagent described above.

That is, the kit may be an adapter ligation kit. A kit refers to a box used to contain chemical reagents for detection of chemical components, drug residues, virus types, etc. The kit here refers to a box containing the adapter ligation reagent.

Beneficial technical effects of the kit in the embodiments of the present disclosure are same as the beneficial technical effects of the adapter in the embodiments of the present disclosure, which will not be repeated here.

Some embodiments of the present disclosure provide an application of the UMI 20 in sequencing a gene. The UMI 20 includes the at the least one random base and the at least one fixed base.

In some embodiments, the gene may include a deoxyribonucleic acid (DNA) molecule or a ribonucleic acid (RNA) molecule for expressing genetic information. UMIs 20 are configured to label different DNA molecules or RNA molecules.

For example, the gene may include a circulating free DNA (cfDNA). The UMIs 20 may be used in the UMI adapters to label different cfDNA molecules.

Some embodiments of the present disclosure provide a method for constructing a DNA library of or a RNA library. The method includes the following steps.

Fragmented DNA is obtained.

The fragmented DNA may be obtained by mechanical breakage or enzymatic hydrolysis.

Of course, before the fragmented DNA is obtained, complementary DNA (cDNA) may be obtained by reverse transcription of mRNA, and the fragmented DNA may be obtained after the cDNA is broken.

In some embodiments, some DNA is cell-free DNA in blood, such as circulating free DNA (cfDNA), which is naturally fragmented and may be directly obtained from the blood or be commercially available. The cfDNA is a kind of DNA that is in a free and cell-free state outside the cell.

End-repair and adenine (A) addition are performed on the fragmented DNA or RNA to obtain end-repair products.

For example, considering an example where the fragmented DNA is cfDNA, end-repair and A addition may be performed on the cfDNA by using a KAPA Biosystem (KAPA) kit.

The end-repaired products are treated with the adapter ligation reagent described above, so that the adapters in the adapter ligation reagent react with the end-repaired products to obtain adapter ligation products.

That is, the above adapter ligation reagent including the plurality of kinds of adapters is used to bind the adapters to the end-repaired products. Each end-repaired product may include a forward strand and a reverse strand. A single end-repaired product may bind with two adapters 10. In a case where each adapter 10 includes a single UMI 20, the adapters 10 are single-ended UMI adapters, which may label different end-repaired products, but may not track forward and reverse strands of the end-repaired products; in a case where the adapters 10 are double-ended UMI adapters, the forward and reverse strands of the end-repaired products may be tracked, so that it may be possible to mark a real mutation in a case where mutated bases at a same position on both the forward and reverse strands appear, which may further improve the detection accuracy.

The adapter ligation products are enriched to obtain the DNA library or the RNA library.

For example, the adapter ligation products may be enriched by PCR amplification.

Since the UMIs 20 in the adapters 10 each include the at least one random base and the at least one fixed base, and the random bases are selected from different bases, the UMIs 20 may label different DNAs depending on the different random bases. In addition, the fixed bases are selected from the known fixed bases, so that it is possible to correct a sequence to be tested and the UMI when the two themselves have errors in amplification or sequencing, which reduces the introduction of false positive mutations.

Some embodiments of the present disclosure provide method for sequencing and detecting a gene. The method includes:

- performing gene sequencing DNA or RNA by using the DNA library or the RNA library obtained by the method for constructing the DNA library or the RNA library described above.

In the embodiments of the present disclosure, since the DNA library or the RNA library obtained by using the method for constructing the DNA library or the RNA library is used for gene sequencing, and DNA molecules or RNA molecules in the DNA library or the RNA library all bind with adapters 10 including UMIs 20, the DNA molecules or the RNA molecules may be labeled by the UMIs 20, and then fixed bases may be used to correct errors generated during sequencing or amplification in a subsequent sequencing process, which may reduce the introduction of false positive mutations and improves the detection accuracy.

Some embodiments of the present disclosure provide a kit. The kit includes: the DNA library or the RNA library obtained by the method for constructing the DNA library or the RNA library described above.

Of course, in some embodiments, the kit may further include a targeted capture kit. The targeted capture kit may include a targeted capture reagent. The targeted capture reagent may perform targeted capture by hybridization or multiplex PCR (which may be performed before an enrichment step in a library construction process), which both allow sequencing of selected genes.

Figure 4:
FIG. 4 is a structural diagram of a unique molecular identifier (UMI) group, in accordance with some embodiments.

Some embodiments of the present disclosure provide a UMI group. As shown in FIG. 4, the UMI group includes: two UMIs 20. The two UMIs 20 bind to each other through complementary pairing of at least a portion of bases thereof. At least one UMI 20 includes at least one random base N and at least one fixed base.

That is, the two UMIs 20 may be located on the first strand 11 and the second strand 12 of the adapter 10. Reference may be made to the above description of the adapter 10 including two UMIs 20, which will not be repeated here.

Figure 5:
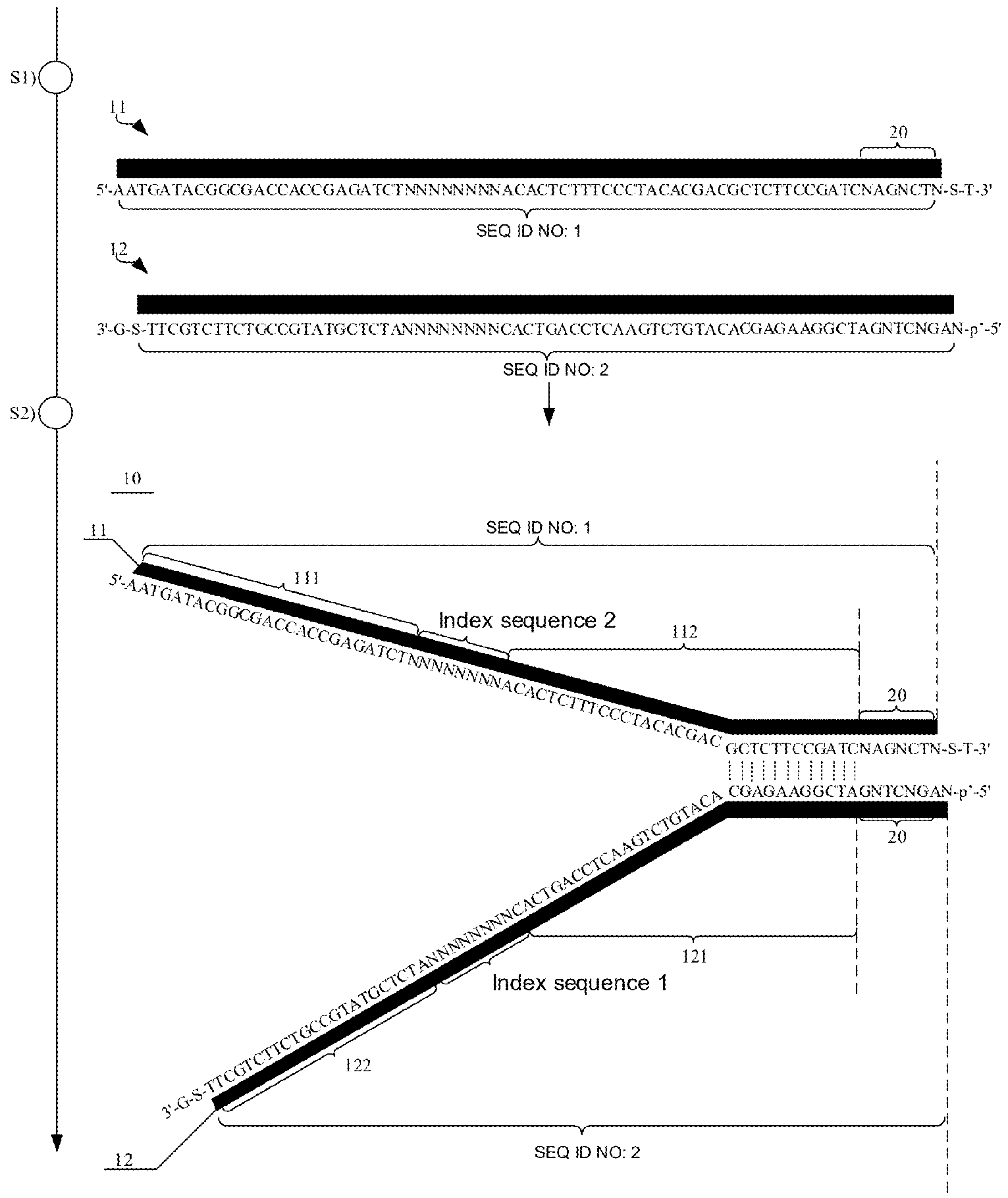
FIG. 5 is a flowchart of a method for preparing an adapter, in accordance with some embodiments.

Some embodiments of the present disclosure provide a method for preparing the adapter 10. The adapter 10 includes the at least one UMI 20. As shown in FIG. 5, the method includes the following steps.

In a step S1), the first strand 11 and the second strand 12 are synthesized. Each UMI 20 is located on the first strand 11 or the second strand 12, and the at least one UMI includes the at least one random base and the at least one fixed base.

For example, the first strand 11 and the second strand 12 may be respectively synthesized by chemical synthesis (i.e., DNA synthesis) rather than by biosynthesis.

Of course, in a case where the UMI group is obtained, a strand (e.g., the first strand 11) and a portion of another strand (e.g., the second strand 12) that is not complementary to the first strand 11 may be synthesized based on the UMI group, and then a portion of the second strand 12 that is complementary to the first strand 11 is synthesized through base complementary pairing.

In a step S2), the first strand 11 and the second strand 12 are annealed to obtain the adapter 10.

That is, when the two single strands, i.e., the first strand 11 and the second strand 12, are synthesized by the above step, the first strand 11 and the second strand 12 may bind to each other through complementary pairing of a portion of bases thereof by specific annealing.

In order to objectively evaluate technical effects of the embodiments of the present disclosure, detailed exemplary description of embodiments of the present application is given through the following embodiments and experimental examples.

1. Adapter Synthesis:

Embodiment 1

In a step 1), 64 first strands 11 and UMI molecular tags 20 located thereon (a UMI 20 located on the first strand 11 being located downstream of a first sequencing primer sequence 112, the UMI 20 including three random bases Ns, and every two random bases N being separated from each other by two fixed bases Ts with a thio-modified end) and 64 second strands 12 and UMI molecular tags 20 located thereon (a UMI 20 located on the second strand 12 being located upstream of a second sequencing primer sequence 121, the UMI 20 including three random bases Ns, every two random bases N are separated from each other by two fixed bases with a phosphate group bound to an end) are synthesized.

A sequence of the first strand 11 is as shown in SEQ ID NO: 1 in a sequence listing, and a sequence of the second strand 12 is as shown in SEQ ID NO: 2 in the sequence listing.

The first strand 11 and the second strand 12 may also be as shown in Table 1 below.

TABLE 1

| | | |
|---|---|---|
| First strand 11 | 5'-aatgatacggcgaccaccgagatctnnnnnnnna cactctttccctacacgacgctcttccgatcnag nctn-st-3' | SEQ ID NO: 1 |
| Second strand 12 | 3'-gs-ttcgtcttctgccgtatgctctannnnn nnncactgacctcaagtctgcacacgagaaggct agntcngan-p'-5' | SEQ ID NO: 2 |

In a case where the Ns of the UMI 20 on the first strand 11 are selected from the four different bases, there are 64 kinds of sequences for UMIs 20 on each of the first strands 11 and the second strands 12. The 64 kinds of sequences for the UMIs 20 are as shown in Table 2 below.

TABLE 2

| UMI sequence for the first strand | | UMI sequence for the second strand | |
|---|---|---|---|
| Name | 5'-3' | Name | 5'-3' |
| SEQ ID NO: 3 | aagacta | SEQ ID NO: 4 | tagtctt |
| SEQ ID NO: 5 | aagactg | SEQ ID NO: 6 | cagtctt |
| SEQ ID NO: 7 | aagactc | SEQ ID NO: 8 | gagtctt |
| SEQ ID NO: 9 | aagactt | SEQ ID NO: 10 | aagtctt |
| SEQ ID NO: 11 | aaggcta | SEQ ID NO: 12 | tagcctt |
| SEQ ID NO: 13 | aaggctg | SEQ ID NO: 14 | cagcctt |
| SEQ ID NO: 15 | aaggctc | SEQ ID NO: 16 | gagcctt |
| SEQ ID NO: 17 | aaggctt | SEQ ID NO: 18 | aagcctt |
| SEQ ID NO: 19 | aagccta | SEQ ID NO: 20 | taggctt |
| SEQ ID NO: 21 | aagcctg | SEQ ID NO: 22 | caggctt |
| SEQ ID NO: 23 | aagcctc | SEQ ID NO: 24 | gaggctt |
| SEQ ID NO: 25 | aagcctt | SEQ ID NO: 26 | aaggctt |
| SEQ ID NO: 27 | aagtcta | SEQ ID NO: 28 | tagactt |
| SEQ ID NO: 29 | aagtctg | SEQ ID NO: 30 | cagactt |
| SEQ ID NO: 31 | aagtctc | SEQ ID NO: 32 | gagactt |
| SEQ ID NO: 33 | aagtctt | SEQ ID NO: 34 | aagactt |
| SEQ ID NO: 35 | gagacta | SEQ ID NO: 36 | tagtctc |
| SEQ ID NO: 37 | gagactg | SEQ ID NO: 38 | cagtctc |
| SEQ ID NO: 39 | gagactc | SEQ ID NO: 40 | gagtctc |
| SEQ ID NO: 41 | gagactt | SEQ ID NO: 42 | aagtctc |
| SEQ ID NO: 43 | gaggcta | SEQ ID NO: 44 | tagcctc |
| SEQ ID NO: 45 | gaggctg | SEQ ID NO: 46 | cagcctc |
| SEQ ID NO: 47 | gaggctc | SEQ ID NO: 48 | gagcctc |
| SEQ ID NO: 49 | gaggctt | SEQ ID NO: 50 | aagcctc |
| SEQ ID NO: 51 | gagccta | SEQ ID NO: 52 | taggctc |
| SEQ ID NO: 53 | gagcctg | SEQ ID NO: 54 | caggctc |
| SEQ ID NO: 55 | gagcctc | SEQ ID NO: 56 | gaggctc |
| SEQ ID NO: 57 | gagcctt | SEQ ID NO: 58 | aaggctc |
| SEQ ID NO: 59 | gagtcta | SEQ ID NO: 60 | tagactc |
| SEQ ID NO: 61 | gagtctg | SEQ ID NO: 62 | cagactc |
| SEQ ID NO: 63 | gagtctc | SEQ ID NO: 64 | gagactc |
| SEQ ID NO: 65 | gagtctt | SEQ ID NO: 66 | aagactc |
| SEQ ID NO: 67 | cagacta | SEQ ID NO: 68 | tagtctg |
| SEQ ID NO: 69 | cagactg | SEQ ID NO: 70 | cagtctg |

TABLE 2-continued

| UMI sequence for the first strand | | UMI sequence for the second strand | |
|---|---|---|---|
| Name | 5'-3' | Name | 5'-3' |
| SEQ ID NO: 71 | cagactc | SEQ ID NO: 72 | gagtctg |
| SEQ ID NO: 73 | cagactt | SEQ ID NO: 74 | aagtctg |
| SEQ ID NO: 75 | caggcta | SEQ ID NO: 76 | tagcctg |
| SEQ ID NO: 77 | caggctg | SEQ ID NO: 78 | cagcctg |
| SEQ ID NO: 79 | caggctc | SEQ ID NO: 80 | gagcctg |
| SEQ ID NO: 81 | caggctt | SEQ ID NO: 82 | aagcctg |
| SEQ ID NO: 83 | cagccta | SEQ ID NO: 84 | taggctg |
| SEQ ID NO: 85 | cagcctg | SEQ ID NO: 86 | caggctg |
| SEQ ID NO: 87 | cagcctc | SEQ ID NO: 88 | gaggctg |
| SEQ ID NO: 89 | cagcctt | SEQ ID NO: 90 | aaggctg |
| SEQ ID NO: 91 | cagtcta | SEQ ID NO: 92 | tagactg |
| SEQ ID NO: 93 | cagtctg | SEQ ID NO: 94 | cagactg |
| SEQ ID NO: 95 | cagtctc | SEQ ID NO: 96 | gagactg |
| SEQ ID NO: 97 | cagtctt | SEQ ID NO: 98 | aagactg |
| SEQ ID NO: 99 | tagacta | SEQ ID NO: 100 | tagtcta |
| SEQ ID NO: 101 | tagactg | SEQ ID NO: 102 | cagtcta |
| SEQ ID NO: 103 | tagactc | SEQ ID NO: 104 | gagtcta |
| SEQ ID NO: 105 | tagactt | SEQ ID NO: 106 | aagtcta |
| SEQ ID NO: 107 | taggcta | SEQ ID NO: 108 | tagccta |
| SEQ ID NO: 109 | taggctg | SEQ ID NO: 110 | cagccta |
| SEQ ID NO: 111 | taggctc | SEQ ID NO: 112 | gagccta |
| SEQ ID NO: 113 | taggctt | SEQ ID NO: 114 | aagccta |
| SEQ ID NO: 115 | tagccta | SEQ ID NO: 116 | taggcta |
| SEQ ID NO: 117 | tagcctg | SEQ ID NO: 118 | caggcta |
| SEQ ID NO: 119 | tagcctc | SEQ ID NO: 120 | gaggcta |
| SEQ ID NO: 121 | tagcctt | SEQ ID NO: 122 | aaggcta |
| SEQ ID NO: 123 | tagtcta | SEQ ID NO: 124 | tagacta |
| SEQ ID NO: 125 | tagtctg | SEQ ID NO: 126 | cagacta |
| SEQ ID NO: 127 | tagtctc | SEQ ID NO: 128 | gagacta |
| SEQ ID NO: 129 | tagtctt | SEQ ID NO: 130 | aagacta |

In a step 2), first strands 11 and second strands 12 paired with each other are resuspended to 100 μM by using 100 μL of a buffer reagent. The buffer reagent includes: 10 mM of trihydroxymethyl aminomethane (Tris) which makes pH of the buffer reagent be 7.5, 2 mM of ethylenediaminetetraacetic acid (EDTA) and 50 mM of NaCl.

In a step 3), 10 μL of the first strands 11, 10 μL of the second strands 12 and 80 μL of the buffer reagent are taken into a PCR tube, mixed well and briefly centrifuged.

In a step 4), the PCR tube is placed in a PCR instrument to react at a program temperature of 95° C. for 10 min; the PCR instrument is turned off after the reaction is completed; and the PCR tube is removed until its temperature drops to room temperature (cooling down about 2 h, the room temperature being about 25° C.).

Figure 6:
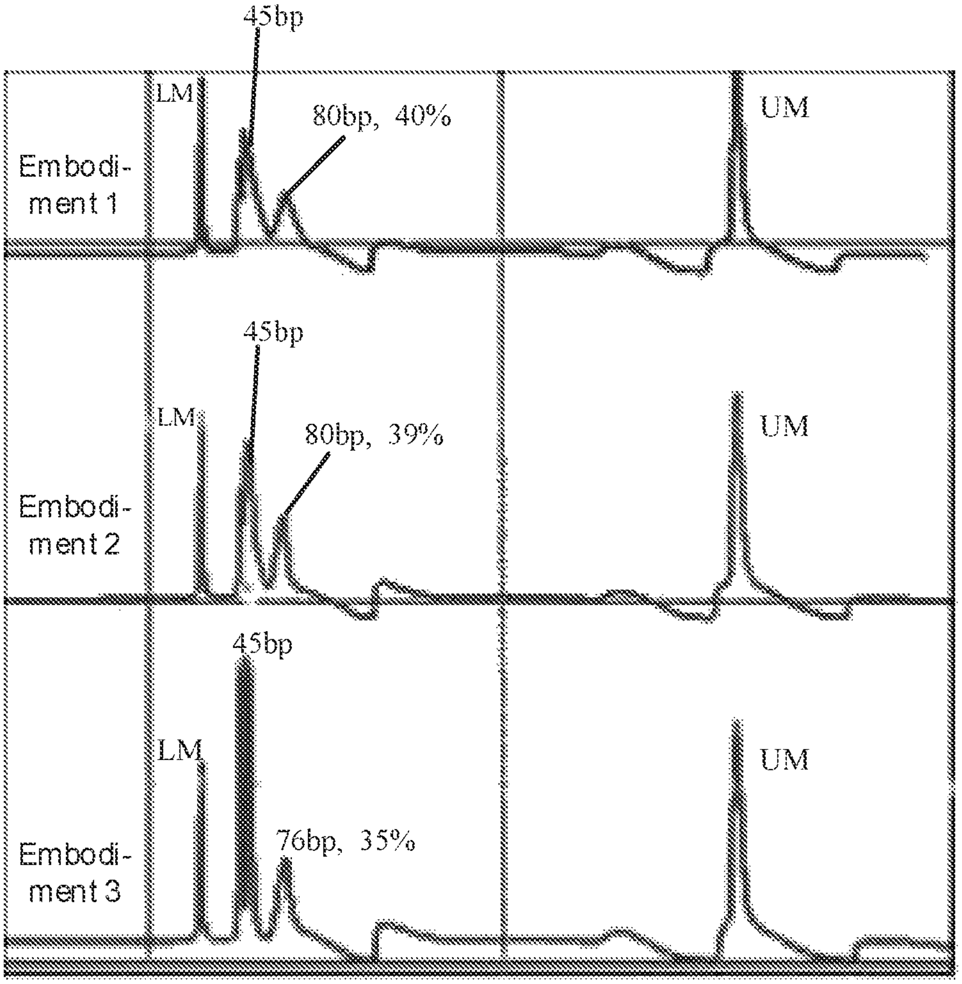
FIG. 6 shows capillary electrophoresis graphs used for detecting synthesis efficiencies of double-stranded adapters of Embodiment 1, Embodiment 2 and Embodiment 3, in accordance with some embodiments.

In a step 5), 1 μL of a sample in the PCR tube is taken to perform quality inspection by an automatic nucleic acid and protein analyzer (Qsep100). The result is as shown in FIG. 6. In FIG. 6, a peak of 70 bp to 80 bp represents a double-strand adapter, LM represents a low marker with a length of 20 bp, UM represents an upper marker with a length of 1000 bp, LM and UM serve as references to mark a position of the double-strand adapter. A synthesis efficiency of adapters may reach about 40%.

Embodiment 2

Steps in Embodiment 2 are substantially same as the steps in Embodiment 1, which will not be repeated here. A difference is that, in a step 1) here, a portion of fixed bases of UMIs on first strands 11 and second strands 12 change.

In Embodiment 2, a sequence of a first strand 11 is as shown in SEQ ID NO: 131 in the sequence listing, and a sequence of a second strand 12 is as shown in SEQ ID NO: 132 in the sequence listing.

The first strand 11 and the second strand 12 may also be as shown in Table 3 below.

TABLE 3

| | | |
|---|---|---|
| First strand 11 | 5'-aatgatacggcgaccaccgagatctnnnnn nnnacactctttccctacacgacgctcttccga tcnagcntagn-st-3' | SEQ ID NO: 131 |
| Second strand 12 | 3'-gs-ttcgtcttctgccgtatgctctannnn nnnncactgacctcaagtctgcacacgagaagg ctagntcgnatcn-p'-5' | SEQ ID NO: 132 |

In a case where the Ns of the UMI 20 on the first strand 11 are selected from the four different bases, there are 64 kinds of sequences for UMIs 20 on each of the first strands 11 and the second strands 12. The 64 kinds of sequences for the UMIs 20 are as shown in Table 4 below.

TABLE 4

| UMI sequence for the first strand | | UMI sequence for the second strand | |
|---|---|---|---|
| Name | 5'-3' | Name | 5'-3' |
| SEQ ID NO: 133 | aagcataga | SEQ ID NO: 134 | tagcttagt |
| SEQ ID NO: 135 | aagcatagg | SEQ ID NO: 136 | cagcttagt |
| SEQ ID NO: 137 | aagcatagc | SEQ ID NO: 138 | gagcttagt |
| SEQ ID NO: 139 | aagcatagt | SEQ ID NO: 140 | aagcttagt |
| SEQ ID NO: 141 | aagcgtaga | SEQ ID NO: 142 | tagcctagt |
| SEQ ID NO: 143 | aagcgtagg | SEQ ID NO: 144 | cagcctagt |
| SEQ ID NO: 145 | aagcgtagc | SEQ ID NO: 146 | gagcctagt |
| SEQ ID NO: 147 | aagcgtagt | SEQ ID NO: 148 | aagcctagt |
| SEQ ID NO: 149 | aagcctaga | SEQ ID NO: 150 | tagcgtagt |
| SEQ ID NO: 151 | aagcctagg | SEQ ID NO: 152 | cagcgtagt |
| SEQ ID NO: 153 | aagcctagc | SEQ ID NO: 154 | gagcgtagt |
| SEQ ID NO: 155 | aagcctagt | SEQ ID NO: 156 | aagcgtagt |

TABLE 4-continued

| UMI sequence for the first strand | | UMI sequence for the second strand | |
|---|---|---|---|
| Name | 5'-3' | Name | 5'-3' |
| SEQ ID NO: 157 | aagcttaga | SEQ ID NO: 158 | tagcatagt |
| SEQ ID NO: 159 | aagcttagg | SEQ ID NO: 160 | cagcatagt |
| SEQ ID NO: 161 | aagcttagc | SEQ ID NO: 162 | gagcatagt |
| SEQ ID NO: 163 | aagcttagt | SEQ ID NO: 164 | aagcatagt |
| SEQ ID NO: 165 | gagcataga | SEQ ID NO: 166 | tagcttagc |
| SEQ ID NO: 167 | gagcatagg | SEQ ID NO: 168 | cagcttagc |
| SEQ ID NO: 169 | gagcatagc | SEQ ID NO: 170 | gagcttagc |
| SEQ ID NO: 171 | gagcatagt | SEQ ID NO: 172 | aagcttagc |
| SEQ ID NO: 173 | gagcgtaga | SEQ ID NO: 174 | tagcctagc |
| SEQ ID NO: 175 | gagcgtagg | SEQ ID NO: 176 | cagcctagc |
| SEQ ID NO: 177 | gagcgtagc | SEQ ID NO: 178 | gagcctagc |
| SEQ ID NO: 179 | gagcgtagt | SEQ ID NO: 180 | aagcctagc |
| SEQ ID NO: 181 | gagcctaga | SEQ ID NO: 182 | tagcgtagc |
| SEQ ID NO: 183 | gagcctagg | SEQ ID NO: 184 | cagcgtagc |
| SEQ ID NO: 185 | gagcctagc | SEQ ID NO: 186 | gagcgtagc |
| SEQ ID NO: 187 | gagcctagt | SEQ ID NO: 188 | aagcgtagc |
| SEQ ID NO: 189 | gagcttaga | SEQ ID NO: 190 | tagcatagc |
| SEQ ID NO: 191 | gagcttagg | SEQ ID NO: 192 | cagcatagc |
| SEQ ID NO: 193 | gagcttagc | SEQ ID NO: 194 | gagcatagc |
| SEQ ID NO: 195 | gagcttagt | SEQ ID NO: 196 | aagcatagc |
| SEQ ID NO: 197 | cagcataga | SEQ ID NO: 198 | tagcttagg |
| SEQ ID NO: 199 | cagcatagg | SEQ ID NO: 200 | cagcttagg |
| SEQ ID NO: 201 | cagcatagc | SEQ ID NO: 202 | gagcttagg |
| SEQ ID NO: 203 | cagcatagt | SEQ ID NO: 204 | aagcttagg |
| SEQ ID NO: 205 | cagcgtaga | SEQ ID NO: 206 | tagcctagg |
| SEQ ID NO: 207 | cagcgtagg | SEQ ID NO: 208 | cagcctagg |
| SEQ ID NO: 209 | cagcgtagc | SEQ ID NO: 210 | gagcctagg |
| SEQ ID NO: 211 | cagcgtagt | SEQ ID NO: 212 | aagcctagg |
| SEQ ID NO: 213 | cagcctaga | SEQ ID NO: 214 | tagcgtagg |
| SEQ ID NO: 215 | cagcctagg | SEQ ID NO: 216 | cagcgtagg |
| SEQ ID NO: 217 | cagcctagc | SEQ ID NO: 218 | gagcgtagg |
| SEQ ID NO: 219 | cagcctagt | SEQ ID NO: 220 | aagcgtagg |
| SEQ ID NO: 221 | cagcttaga | SEQ ID NO: 222 | tagcatagg |
| SEQ ID NO: 223 | cagcttagg | SEQ ID NO: 224 | cagcatagg |
| SEQ ID NO: 225 | cagcttagc | SEQ ID NO: 226 | gagcatagg |
| SEQ ID NO: 227 | cagcttagt | SEQ ID NO: 228 | aagcatagg |
| SEQ ID NO: 229 | tagcataga | SEQ ID NO: 230 | tagcttaga |
| SEQ ID NO: 231 | tagcatagg | SEQ ID NO: 232 | cagcttaga |

TABLE 4-continued

| UMI sequence for the first strand | | UMI sequence for the second strand | |
|---|---|---|---|
| Name | 5'-3' | Name | 5'-3' |
| SEQ ID NO: 233 | tagcatagc | SEQ ID NO: 234 | gagcttaga |
| SEQ ID NO: 235 | tagcatagt | SEQ ID NO: 236 | aagcttaga |
| SEQ ID NO: 237 | tagcgtaga | SEQ ID NO: 238 | tagcctaga |
| SEQ ID NO: 239 | tagcgtagg | SEQ ID NO: 240 | cagcctaga |
| SEQ ID NO: 241 | tagcgtagc | SEQ ID NO: 242 | gagcctaga |
| SEQ ID NO: 243 | tagcgtagt | SEQ ID NO: 244 | aagcctaga |
| SEQ ID NO: 245 | tagcctaga | SEQ ID NO: 246 | tagcgtaga |
| SEQ ID NO: 247 | tagcctagg | SEQ ID NO: 248 | cagcgtaga |
| SEQ ID NO: 249 | tagcctagc | SEQ ID NO: 250 | gagcgtaga |
| SEQ ID NO: 251 | tagcctagt | SEQ ID NO: 252 | aagcgtaga |
| SEQ ID NO: 253 | tagcttaga | SEQ ID NO: 254 | tagcataga |
| SEQ ID NO: 255 | tagcttagg | SEQ ID NO: 256 | cagcataga |
| SEQ ID NO: 257 | tagcttagc | SEQ ID NO: 258 | gagcataga |
| SEQ ID NO: 259 | tagcttagt | SEQ ID NO: 260 | aagcataga |

Embodiment 3

Steps in Embodiment 3 are substantially same as the steps in Embodiment 1, which will not be repeated here. A difference is that, in a step 1) here, a portion of fixed bases of UMIs in first strands 11 and second strands 12 change.

In Embodiment 3, a sequence of a first strand 11 is as shown in SEQ ID NO: 261 in the sequence listing, and a sequence of a second strand 12 is as shown in SEQ ID NO: 262 in the sequence listing.

The first strand 11 and the second strand 12 may also be as shown in Table 5 below.

TABLE 5

| | | |
|---|---|---|
| First strand 11 | 5'-aatgatacggcgaccaccgagatctnnnnn nnnacactctttccctacacgacgctcttccga tcnagctnagctn-st-3' | SEQ ID NO: 261 |
| Second strand | 3'-gs-ttcgtcttctgccgtatgctctannnn nnnncactgacctcaagtctgcacacgagaagg ctagntcga12ntcgan-p'-5' | SEQ ID NO: 262 |

In a case where the Ns of the UMI 20 in the first strand 11 are selected from the four different bases, there are 64 kinds of sequences for UMIs 20 on first strands 11 and second strands 12. The 64 kinds of sequences of the UMI 20 are as shown in Table 6 below.

TABLE 6

| UMI sequence for the first strand | | UMI sequence for the second strand | |
|---|---|---|---|
| Name | 5'-3' | Name | 5'-3' |
| SEQ ID NO: 263 | aagctaagcta | SEQ ID NO: 264 | tagcttagctt |
| SEQ ID NO: 265 | aagctaagctg | SEQ ID NO: 266 | cagcttagctt |
| SEQ ID NO: 267 | aagctaagctc | SEQ ID NO: 268 | gagcttagctt |
| SEQ ID NO: 269 | aagctaagctt | SEQ ID NO: 270 | aagcttagctt |
| SEQ ID NO: 271 | aagctgagcta | SEQ ID NO: 272 | tagctcagctt |
| SEQ ID NO: 273 | aagctgagctg | SEQ ID NO: 274 | cagctcagctt |
| SEQ ID NO: 275 | aagctgagctc | SEQ ID NO: 276 | gagctcagctt |
| SEQ ID NO: 277 | aagctgagctt | SEQ ID NO: 278 | aagctcagctt |
| SEQ ID NO: 279 | aagctcagcta | SEQ ID NO: 280 | tagctgagctt |
| SEQ ID NO: 281 | aagctcagctg | SEQ ID NO: 282 | cagctgagctt |
| SEQ ID NO: 283 | aagctcagctc | SEQ ID NO: 284 | gagctgagctt |
| SEQ ID NO: 285 | aagctcagctt | SEQ ID NO: 286 | aagctgagctt |
| SEQ ID NO: 287 | aagcttagcta | SEQ ID NO: 288 | tagctaagctt |
| SEQ ID NO: 289 | aagcttagctg | SEQ ID NO: 290 | cagctaagctt |
| SEQ ID NO: 291 | aagcttagctc | SEQ ID NO: 292 | gagctaagctt |
| SEQ ID NO: 293 | aagcttagctt | SEQ ID NO: 294 | aagctaagctt |
| SEQ ID NO: 295 | gagctaagcta | SEQ ID NO: 296 | tagcttagctc |
| SEQ ID NO: 297 | gagctaagctg | SEQ ID NO: 298 | cagcttagctc |
| SEQ ID NO: 299 | gagctaagctc | SEQ ID NO: 300 | gagcttagctc |
| SEQ ID NO: 301 | gagctaagctt | SEQ ID NO: 302 | aagcttagctc |
| SEQ ID NO: 303 | gagctgagcta | SEQ ID NO: 304 | tagctcagctc |
| SEQ ID NO: 305 | gagctgagctg | SEQ ID NO: 306 | cagctcagctc |
| SEQ ID NO: 307 | gagctgagctc | SEQ ID NO: 308 | gagctcagctc |
| SEQ ID NO: 309 | gagctgagctt | SEQ ID NO: 310 | aagctcagctc |
| SEQ ID NO: 311 | gagctcagcta | SEQ ID NO: 312 | tagctgagctc |
| SEQ ID NO: 313 | gagctcagctg | SEQ ID NO: 314 | cagctgagctc |
| SEQ ID NO: 315 | gagctcagctc | SEQ ID NO: 316 | gagctgagctc |
| SEQ ID NO: 317 | gagctcagctt | SEQ ID NO: 318 | aagctgagctc |
| SEQ ID NO: 319 | gagcttagcta | SEQ ID NO: 320 | tagctaagctc |
| SEQ ID NO: 321 | gagcttagctg | SEQ ID NO: 322 | cagctaagctc |
| SEQ ID NO: 323 | gagcttagctc | SEQ ID NO: 324 | gagctaagctc |
| SEQ ID NO: 325 | gagcttagctt | SEQ ID NO: 326 | aagctaagctc |
| SEQ ID NO: 327 | cagctaagcta | SEQ ID NO: 328 | tagcttagctg |
| SEQ ID NO: 329 | cagctaagctg | SEQ ID NO: 330 | cagcttagctg |
| SEQ ID NO: 331 | cagctaagctc | SEQ ID NO: 332 | gagcttagctg |
| SEQ ID NO: 333 | cagctaagctt | SEQ ID NO: 334 | aagcttagctg |
| SEQ ID NO: 335 | cagctgagcta | SEQ ID NO: 336 | tagctcagctg |
| SEQ ID NO: 337 | cagctgagctg | SEQ ID NO: 338 | cagctcagctg |

TABLE 6-continued

| UMI sequence for the first strand | | UMI sequence for the second strand | |
|---|---|---|---|
| Name | 5'-3' | Name | 5'-3' |
| SEQ ID NO: 339 | cagctgagctc | SEQ ID NO: 340 | gagctcagctg |
| SEQ ID NO: 341 | cagctgagctt | SEQ ID NO: 342 | aagctcagctg |
| SEQ ID NO: 343 | cagctcagcta | SEQ ID NO: 344 | tagctgagctg |
| SEQ ID NO: 345 | cagctcagctg | SEQ ID NO: 346 | cagctgagctg |
| SEQ ID NO: 347 | cagctcagctc | SEQ ID NO: 348 | gagctgagctg |
| SEQ ID NO: 349 | cagctcagctt | SEQ ID NO: 350 | aagctgagctg |
| SEQ ID NO: 351 | cagcttagcta | SEQ ID NO: 352 | tagctaagctg |
| SEQ ID NO: 353 | cagcttagctg | SEQ ID NO: 354 | cagctaagctg |
| SEQ ID NO: 355 | cagcttagctc | SEQ ID NO: 356 | gagctaagctg |
| SEQ ID NO: 357 | cagcttagctt | SEQ ID NO: 358 | aagctaagctg |
| SEQ ID NO: 359 | tagctaagcta | SEQ ID NO: 360 | tagcttagcta |
| SEQ ID NO: 361 | tagctaagctg | SEQ ID NO: 362 | cagcttagcta |
| SEQ ID NO: 363 | tagctaagctc | SEQ ID NO: 364 | gagcttagcta |
| SEQ ID NO: 365 | tagctaagctt | SEQ ID NO: 366 | aagcttagcta |
| SEQ ID NO: 367 | tagctgagcta | SEQ ID NO: 368 | tagctcagcta |
| SEQ ID NO: 369 | tagctgagctg | SEQ ID NO: 370 | cagctcagcta |
| SEQ ID NO: 371 | tagctgagctc | SEQ ID NO: 372 | gagctcagcta |
| SEQ ID NO: 373 | tagctgagctt | SEQ ID NO: 374 | aagctcagcta |
| SEQ ID NO: 375 | tagctcagcta | SEQ ID NO: 376 | tagctgagcta |
| SEQ ID NO: 377 | tagctcagctg | SEQ ID NO: 378 | cagctgagcta |
| SEQ ID NO: 379 | tagctcagctc | SEQ ID NO: 380 | gagctgagcta |
| SEQ ID NO: 381 | tagctcagctt | SEQ ID NO: 382 | aagctgagcta |
| SEQ ID NO: 383 | tagcttagcta | SEQ ID NO: 384 | tagctaagcta |
| SEQ ID NO: 385 | tagcttagctg | SEQ ID NO: 386 | cagctaagcta |
| SEQ ID NO: 387 | tagcttagctc | SEQ ID NO: 388 | gagctaagcta |
| SEQ ID NO: 389 | tagcttagctt | SEQ ID NO: 390 | aagctaagcta |

2. Library Construction and Sequencing:

Experimental Example 1

In a step 1), the cfDNA standards with a plurality of mutation sites and mutation frequencies of 1% and 0.1% customized from GeneWell are used as samples. The used standards are cfDNA samples, which do not need to be fragmented and may be directly used for constructing a library.

In a step 2), end repair and A addition are performed on the cfDNA by using a KAPA kit.

In a step 3), the cfDNA is bound with adapters by using a KAPA kit and the adapters synthesized in Embodiments 1, so as to obtain adapter ligation products.

In a step 4), the adapter ligation products are amplified, enriched and purified to obtain a cfDNA library.

In a step 5), targeted capture is performed on the adapter ligation products by using a complete kit of Integrated DNA Technologies (IDT) to obtain adapter ligation products of selected gene.

In a step 6), sequencing on a computer is performed by using the cfDNA library obtained in the step 4) as samples and by using a Novaseq 6000 (Illumina) instrument according to a routine use of the instrument.

In a step 7), the FastQC software is used to analyze basic quality control of offline data. Actual detected sites and mutations are substantially consistent with theoretical values. Specific detection results are as shown in Tables 7 and 8 below.

Experimental Example 2

Steps in Experimental example 2 are substantially same as the steps in Experimental example 1, which will not be repeated here. A difference is that, adapters synthesized in Embodiment 2 are used for constructing a library in a step 3) here. Actual detected sites and mutations are also substantially consistent with the theoretical values. Specific detection results are as shown in Tables 7 and 8 below.

Experimental Example 3

Steps in Experimental example 3 are substantially same as the steps in Experimental example 1, which will not be repeated here. A difference is that, adapters synthesized in Embodiment 3 are used for library construction in a step 3) here. Actual detected sites and mutations are also substantially consistent with the theoretical values. Specific detection results are as shown in Tables 7 and 8 below.

TABLE 7

| Experimental example | Gene | Mutation site | Theoretical mutation frequency | Actually detected mutation frequency |
|---|---|---|---|---|
| Experimental Example 1 | EGFR | T790M | 0.1% | 0.091% |
| | EGFR | L858R | 0.1% | 0.110% |
| | KRAS | G12D | 0.1% | 0.120% |
| | NRAS | Q61K | 0.1% | 0.089% |
| Experimental example 2 | EGFR | T790M | 0.1% | 0.095% |
| | KRAS | G12D | 0.1% | 0.100% |
| | KRAS | G13D | 0.1% | 0.150% |
| | NRAS | Q61K | 0.1% | 0.081% |
| Experimental example 3 | EGFR | T790M | 0.1% | 0.092% |
| | KRAS | G12D | 0.1% | 0.130% |
| | KRAS | G13D | 0.1% | 0.140% |
| | NRAS | Q61K | 0.1% | 0.079% |

TABLE 8

| Experimental example | Gene | Mutation site | Theoretical mutation frequency | Actually detected mutation frequency |
|---|---|---|---|---|
| Experimental example 1 | EGFR | T790M | 1% | 1.20% |
| | EGFR | L858R | 1% | 1.11% |
| | KRAS | G12D | 1% | 0.91% |
| | NRAS | Q61K | 1% | 0.80% |
| Experimental example 2 | EGFR | T790M | 1% | 1.30% |
| | KRAS | G12D | 1% | 0.93% |
| | KRAS | G13D | 1% | 0.98% |
| | NRAS | Q61K | 1% | 0.85% |

TABLE 8-continued

| Experimental example | Gene | Mutation site | Theoretical mutation frequency | Actually detected mutation frequency |
|---|---|---|---|---|
| Experimental example 3 | EGFR | T790M | 1% | 1.25% |
| | KRAS | G12D | 1% | 1.01% |
| | KRAS | G13D | 1% | 0.95% |
| | NRAS | Q61K | 1% | 0.78% |

In Table 7, the actually detected mutation frequencies of the different mutation sites of the selected genes in Experimental example 1 are substantially between 0.089% to 0.12%, which are relatively accurate compared with the theoretical mutation frequency (0.1%): the actually detected mutation frequencies of the different mutation sites of the selected genes in Experimental example 2 are substantially between 0.081% to 0.150%, which are also relatively accurate compared with the theoretical mutation frequency; and the actually detected mutation frequencies of the different mutation sites of the selected genes in Experimental example 3 are substantially between 0.079% to 0.140%, which are still relatively accurate compared with the theoretical mutation frequency.

In Table 8, the actually detected mutation frequencies of the different mutation sites of the selected genes in Experimental example 1 are substantially between 0.80% to 1.20%, which are relatively accurate compared with the theoretical mutation frequency (1%); the actually detected mutation frequencies of the different mutation sites of the selected genes in Experimental example 2 are substantially between 0.85% to 1.30%, which are also relatively accurate compared with the theoretical mutation frequency; and the actually detected mutation frequencies of the different mutation sites of the selected genes in Experimental example 3 are substantially between 0.78% to 1.25%, which are still relatively accurate compared with the theoretical mutation frequency.

To sum up, by using the UMIs partially composed of fixed bases, it may be possible to ensure the diversity of the adapters to label the different original DNA fragments; and moreover, the noise mutations introduced by PCR amplification or sequencing may be avoided to a certain extent, which improves the detection accuracy.

The foregoing descriptions are merely specific implementations of the present disclosure. However, the protection scope of the present disclosure is not limited thereto. Changes or replacements that any person skilled in the art could conceive of within the technical scope of the present disclosure shall be included in the protection scope of the present disclosure. Therefore, the protection scope of the present disclosure shall be subject to the protection scope of the claims.

What is claimed is:

1. A unique molecular identifier (UMI), comprising:

at least one random base and at least one fixed base; wherein the at least one random base includes three random bases, the at least one fixed bases includes a plurality of fixed bases;

at least two random bases of the three random bases are arranged at intervals, and/or at least two fixed bases of the plurality of fixed bases are arranged at intervals; and a sequence of the UMI is one of SEQ ID NO:3 to SEQ ID NO: 130, or one of SEQ ID NO: 133 to SEQ ID NO:260, or one of SEQ ID NO:263 to SEQ ID NO:390.

2. The UMI according to claim 1, wherein in a case where the at least two random bases of the three random bases are arranged at intervals, every two random bases arranged at intervals are separated by one to five fixed bases.

3. The UMI according to claim 2, wherein every two of the three random bases are arranged at intervals from each other and separated by a group of fixed bases, and every two groups of fixed bases each include a same number of fixed bases.

4. The UMI according to claim 3, wherein for the every two adjacent groups of fixed bases, at least one fixed base of one group of fixed bases is different from a fixed base of another group of fixed bases.

5. The UMI according to claim 2, wherein the every two random bases arranged at intervals are separated by 2 to 4 fixed bases, and the 2 to 4 fixed bases are different from each other.

6. The UMI according to claim 1, wherein the UMI comprises 7, 9 or 11 bases.

7. A molecular identifier group, comprising:

two unique molecular identifiers (UMIs) binding to each other through complementary pairing of at least a portion of bases thereof, wherein at least one UMI is the UMI according to claim 1.

8. An adapter, comprising:

a first strand and a second strand; and at least one unique molecular identifier (UMI), each UMI being located on the first strand or the second strand, the at least one UMI being the UMI according to claim 1.

9. The adapter according to claim 8, wherein the at least one UMI includes two UMIs; the two UMIs are respectively located on the first strand and the second strand, and bind to each other through complementary pairing of at least a portion of bases thereof.

10. The adapter according to claim 9, wherein the first strand is a forward strand, and the second strand is a reverse strand, wherein the first strand includes a first sequencing primer sequence; the second strand includes a second sequencing primer sequence; a UMI located on the first strand is located downstream of the first sequencing primer sequence; and a UMI located on the second strand is located upstream of the second sequencing primer sequence.

11. An adapter ligation reagent, comprising:

a plurality of kinds of adapters, the plurality of kinds of adapters being each the adapter according to claim 8, wherein of the plurality of kinds of adapters, for every two kinds of adapters, at least one random base of at least one UMI included in one kind of adapter is different from at least one random base of at least one UMI included in another kind of adapter.

12. A kit, comprising:

the adapter ligation reagent according to claim 11.

* * * * *